(12) United States Patent
Tullous

(10) Patent No.: US 8,590,536 B2
(45) Date of Patent: Nov. 26, 2013

(54) LATERAL SUPPORT CRANIOCERVICAL ORTHOSIS AND METHOD

(76) Inventor: Micam W. Tullous, San Antonio, TX (US)

( * ) Notice: Subject to any disclaimer, the term of this patent is extended or adjusted under 35 U.S.C. 154(b) by 0 days.

(21) Appl. No.: 12/864,103

(22) PCT Filed: Feb. 19, 2010

(86) PCT No.: PCT/US2010/024838
§ 371 (c)(1),
(2), (4) Date: Jul. 22, 2010

(87) PCT Pub. No.: WO2010/096727
PCT Pub. Date: Aug. 26, 2010

(65) Prior Publication Data
US 2011/0108040 A1    May 12, 2011

Related U.S. Application Data

(63) Continuation-in-part of application No. 12/389,320, filed on Feb. 19, 2009, now abandoned, which is a continuation-in-part of application No. 11/449,402, filed on Jun. 8, 2006, now abandoned.

(51) Int. Cl.
*A61G 15/00* (2006.01)

(52) U.S. Cl.
USPC ........................ 128/845; 5/636; 5/637; 5/655

(58) Field of Classification Search
USPC .............. 128/846, 870, 845; 5/622, 636–637, 5/640, 655; 602/17
See application file for complete search history.

(56) References Cited

U.S. PATENT DOCUMENTS

| | | | |
|---|---|---|---|
| 2,876,459 A | 3/1959 | Ackerson | |
| 3,877,093 A | 4/1975 | Gershbein | |
| 4,218,792 A * | 8/1980 | Kogan | ............................. 5/636 |
| 4,383,713 A | 5/1983 | Roston | |
| 4,631,766 A * | 12/1986 | Semmler et al. | .................. 5/655 |
| 4,776,324 A | 10/1988 | Clarren | |
| 4,825,487 A | 5/1989 | Eberl | |

(Continued)

FOREIGN PATENT DOCUMENTS

| | | |
|---|---|---|
| DE | 20 2005 019 550 U1 | 4/2007 |
| EP | 0 880 925 A1 | 12/1998 |

(Continued)

OTHER PUBLICATIONS

Instruction Manual for Sleep Guard Mattress.

(Continued)

*Primary Examiner* — Patricia Bianco
*Assistant Examiner* — Camtu Nguyen

(57) ABSTRACT

A device and method for preventing and correcting abnormal shaping of an infant's cranium by applying external forces over time with the growth of an infant to achieve normal shaping of the infant's head. The device is a cranial orthosis having a depression with a contact surface in the shape of at least a portion of a normal infantile cranium. The orthosis further provides lateral support surfaces creating points of contact to restrict rotation of the infant's cranium and provide additional external forces for normal shaping of the infant's cranium. Because the present invention is non-conforming to the shape of an abnormal skull, the exerted forces cause accelerated expansion of the skull in less prominent areas coincident with brain and skull growth.

48 Claims, 26 Drawing Sheets

(56) References Cited

U.S. PATENT DOCUMENTS

| | | |
|---|---|---|
| 5,048,136 A | 9/1991 | Pipitz |
| 5,127,120 A * | 7/1992 | Mason ............................... 5/655 |
| 5,360,017 A | 11/1994 | Austin |
| 5,423,099 A | 6/1995 | Gulli |
| 5,524,640 A | 6/1996 | Lisak |
| 5,566,413 A | 10/1996 | Webb |
| 5,709,649 A | 1/1998 | Chitwood |
| 5,743,271 A | 4/1998 | Royo-Salvador |
| 5,820,573 A | 10/1998 | Ramos |
| 6,052,849 A | 4/2000 | Dixon |
| 6,088,855 A | 7/2000 | Connolly |
| 6,321,403 B1 | 11/2001 | Matthews |
| 6,446,288 B1 | 9/2002 | Pi |
| 6,473,923 B1 | 11/2002 | Straub |
| 6,536,058 B1 | 3/2003 | Chang |
| 6,592,536 B1 | 7/2003 | Argenta |
| 6,848,134 B1 | 2/2005 | Schenck |
| 6,915,598 B2 * | 7/2005 | Grisoni et al. .................. 36/151 |
| 7,234,181 B1 | 6/2007 | Griggs |
| 7,418,752 B2 | 9/2008 | Kemm |
| 7,556,607 B2 | 7/2009 | Coates |
| 7,647,660 B2 | 1/2010 | Tullous |
| 7,810,501 B2 | 10/2010 | Rogers |
| 2002/0153753 A1 | 10/2002 | Kassai |
| 2002/0174488 A1 | 11/2002 | Appleton |
| 2003/0033674 A1 | 2/2003 | Mann |

FOREIGN PATENT DOCUMENTS

| | | |
|---|---|---|
| EP | 1 557 117 A1 | 7/2005 |
| EP | 1 202 654 B1 | 11/2005 |
| EP | 1 864 595 A1 | 7/2007 |
| EP | 1 665 958 A1 | 12/2007 |
| EP | 1864630 | 12/2007 |
| ES | 2 241 617 | 8/2002 |
| FR | 2 859 615 | 3/2005 |
| GB | 2 412 062 A | 9/2005 |
| JP | 48019774 | 6/1973 |
| NZ | 51042 A | 1/2004 |
| WO | 01/00064 A1 | 1/2001 |
| WO | 2005/025385 A1 | 3/2005 |
| WO | 2005/092154 A1 | 10/2005 |
| WO | 2006102407 | 9/2006 |

OTHER PUBLICATIONS

Memory Foam Kids Pillow (www.onestepahead.com web page).
Photos of Computed Tomography (CT) Scan Pillow.
Photos of Cerebrial Angiogram/Arterioaram Positioning Headrest.

* cited by examiner

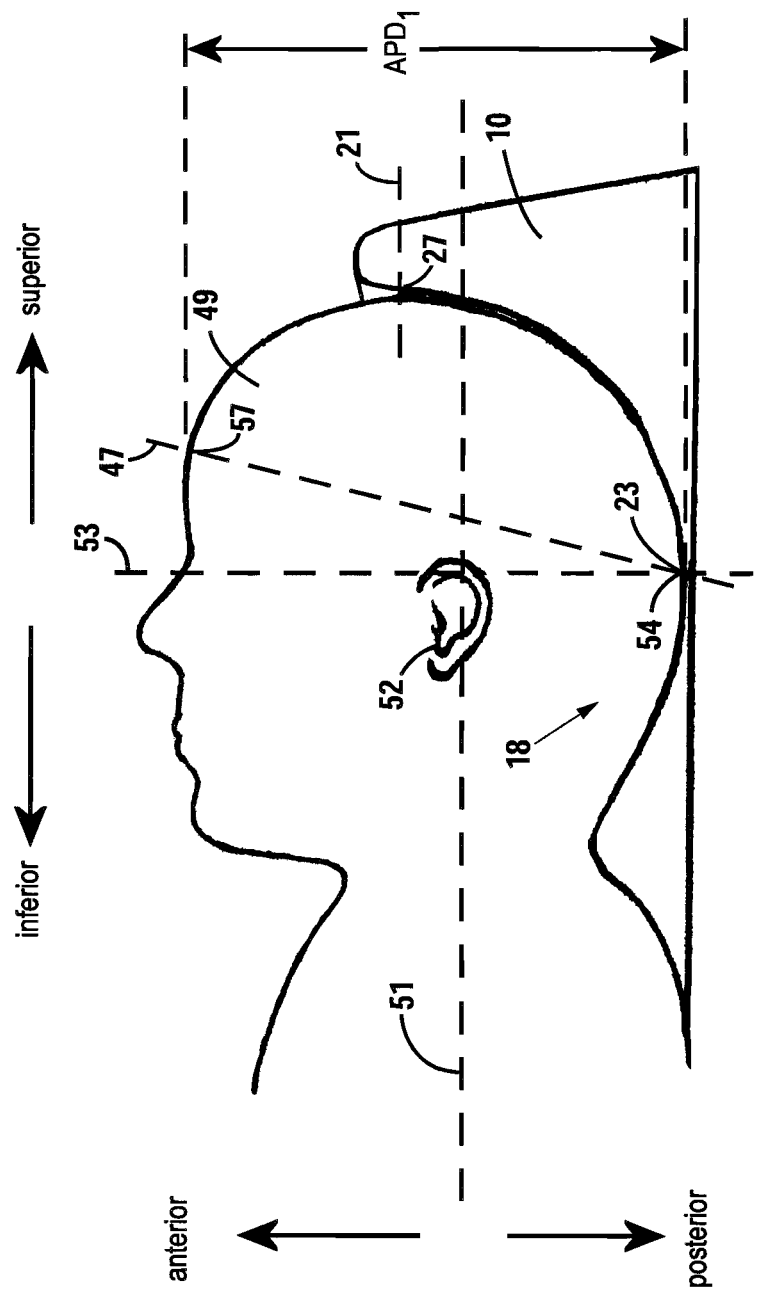

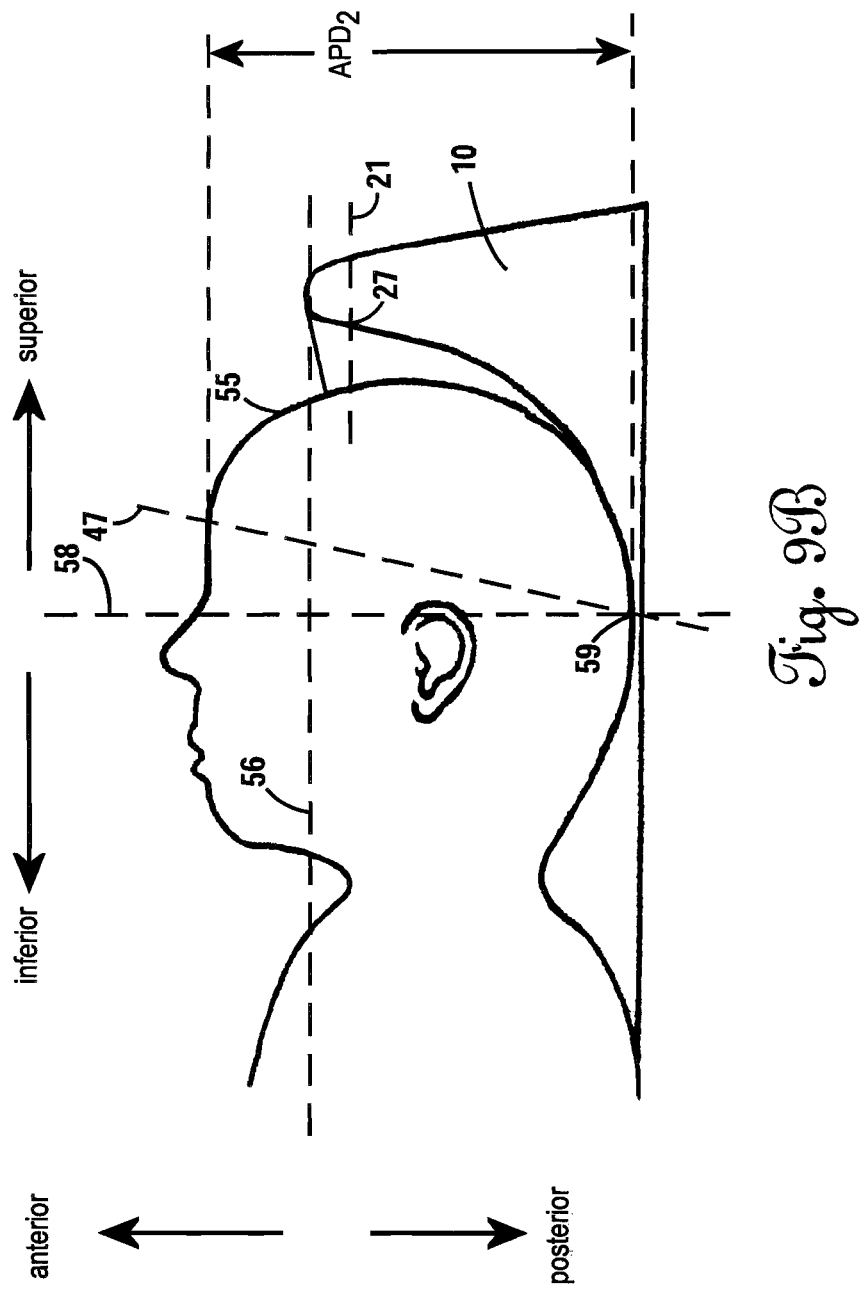

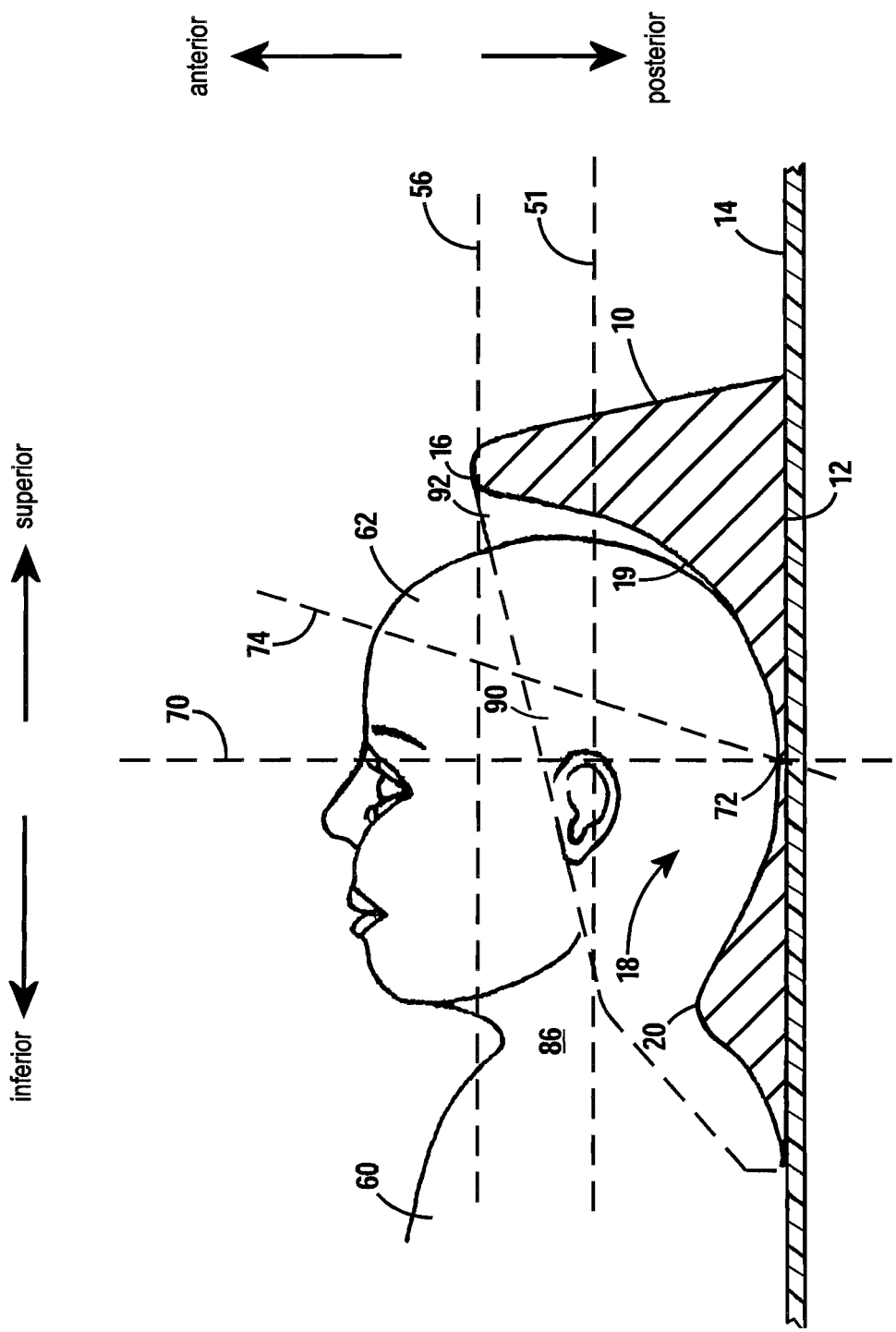

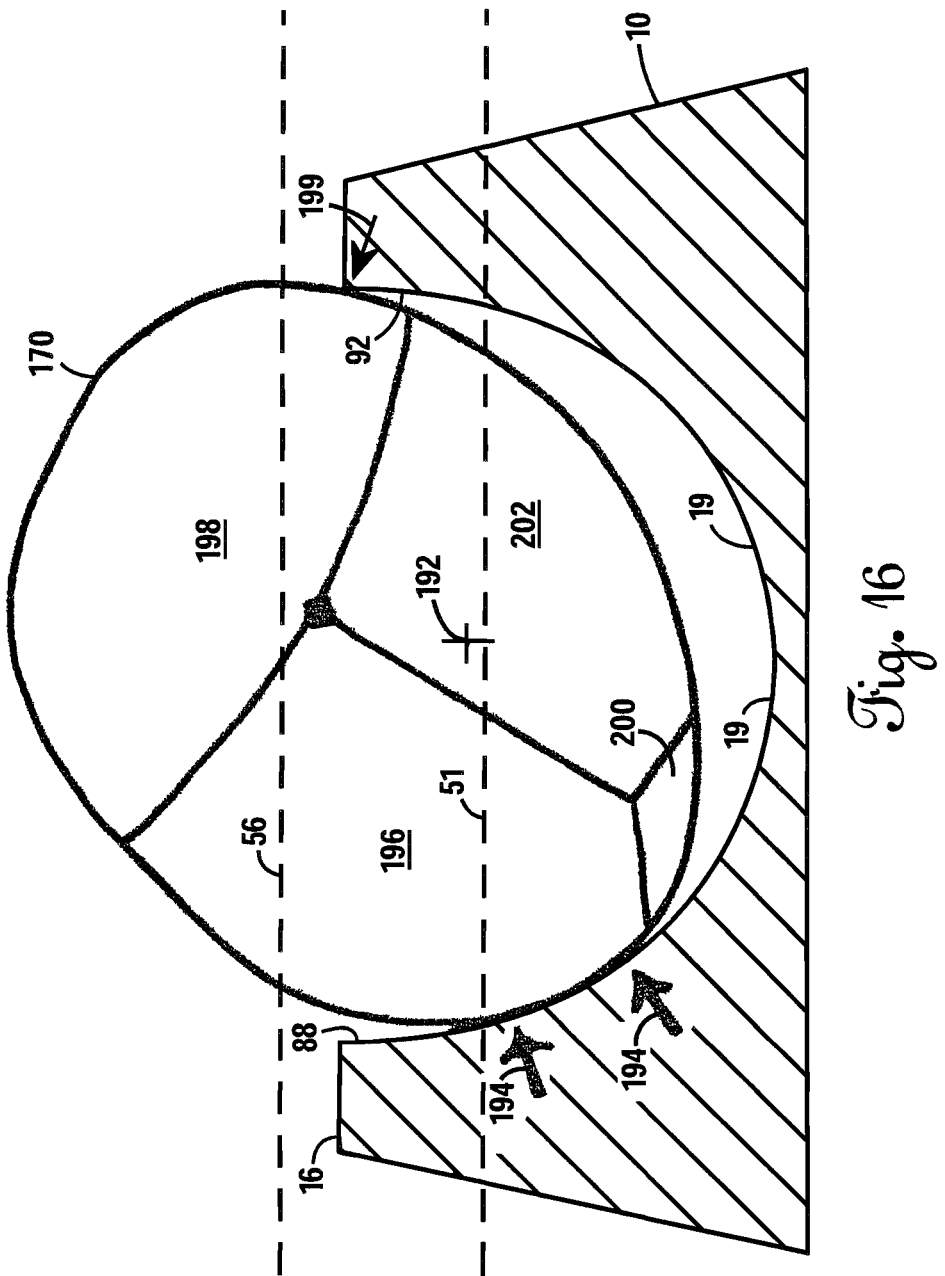

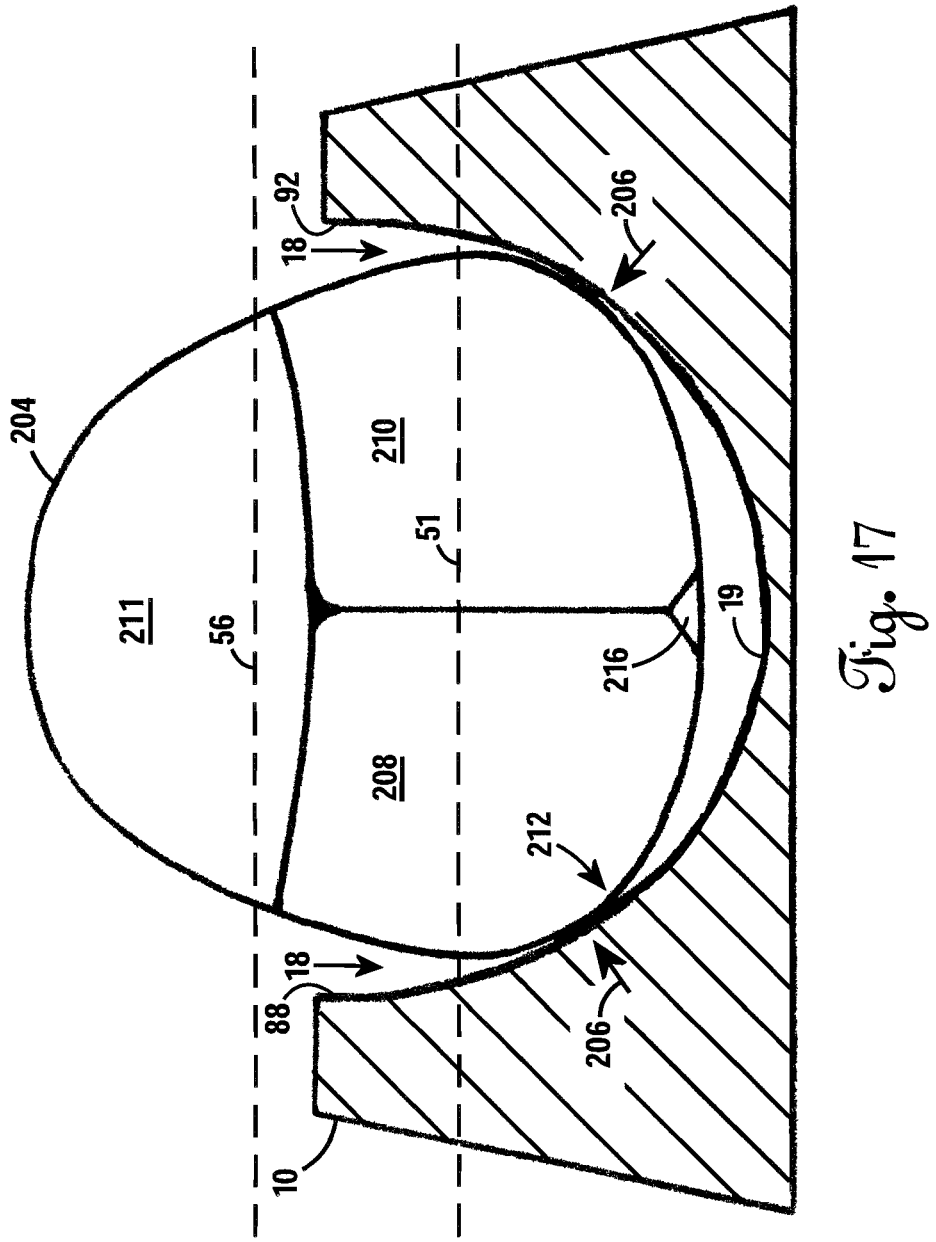

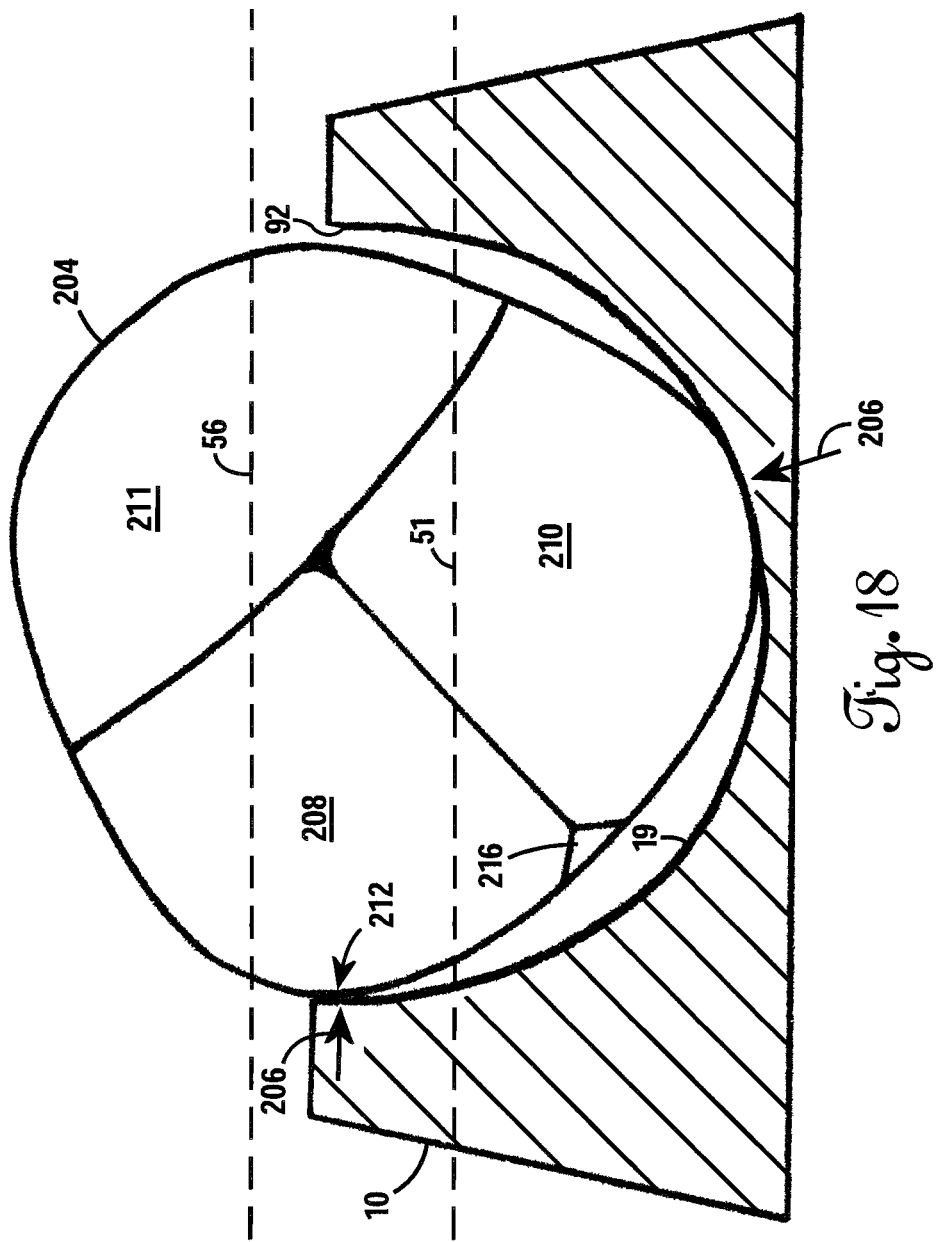

LATERAL SUPPORT CRANIOCERVICAL ORTHOSIS AND METHOD

CROSS-REFERENCES TO RELATED APPLICATIONS

This is a continuation-in-part application that claims the benefit of U.S. patent application Ser. No. 12/389,320, filed Feb. 19, 2009 and entitled "Lateral Support Craniocervical Orthosis and Method," which is a continuation-in-part application that claims the benefit of U.S. patent application Ser. No. 11/449,402, filed Jun. 8, 2006 and entitled "Headrest and Method for Correcting Non-Synostotic Cranial Deformities in Infants." Each of these applications is incorporated by reference herein.

STATEMENT REGARDING FEDERALLY-SPONSORED RESEARCH OR DEVELOPMENT

Not applicable.

BACKGROUND OF THE INVENTION

1. Field of the Invention

The present invention relates generally to a craniocervical orthosis in which an infant's cranium is positioned while the infant is sleeping to prevent and correct cranial deformities. More specifically, the invention relates to a craniocervical orthosis and method for preventing and correcting any non-synostotic deformity of the side and posterior aspects of an infant's head.

2. Background of the Invention

At birth, the six cranial bones comprising an infant's skull are spaced far enough apart to allow the skull to rapidly grow during the first months of the infant's life. This spacing also allows the bones to overlap so the infant's head can pass through the birth canal without compressing, and thereby damaging, the infant's brain. Eventually—some time between three and six years of age—the cranial bones will fuse and remain fused for the rest of the child's life.

During an infant's normal growth, forces within the infant's skull are directed outward and are constant and equally distributed on the inner surface of the growing skull causing the skull to expand. Accordingly, a decrease of the intracranial pressure will cause a reduced head size. Similarly, an increase in intracranial pressure will cause an increased head size.

Fibrous bands of tissue, called cranial sutures, fill the space between the bones and connect the bones of the skull to each other. These cranial sutures are strong and elastic, providing a flexibility to the skull to allow rapid brain growth during the first months of life. Without the sutures, a child would suffer brain damage due to constriction of the brain during the period of normal growth.

During the first few months of an infants' life, however, the infant is most susceptible to the formation of synostotic or non-synostotic deformities in the cranium. Synostotic deformities are a result of craniosynostosis, which is a birth defect of the skull characterized by premature closure of one or more of the cranial sutures. Craniosynostosis can be hereditary or the result of a metabolic disease, and is characterized by an abnormally-shaped skull and potential for abnormal intracranial pressure, mental retardation, seizures, and blindness.

On the other hand, non-synostotic deformities, in which the cranial sutures remain open, are caused by environmental conditions, including premature birth, torticollis (twisting of the neck muscles beyond their normal position), or the preferred sleeping position of the child. In addition, neurological abnormalities, such as paralysis, cerebral palsy, or some sort of developmental delay, may predispose a child to cranial positioning problems. Non-synostotic deformities are also called positional deformities.

Synostotic and non-synostotic deformities manifest themselves in a variety of ways. Plagiocephaly, for example, is a cranial deformity resulting in an asymmetric head shape. Plagiocephaly consists of a focal area of flattening in the anterior or posterior aspect of one side of the head, which also commonly produces additional compensatory deformities in adjacent areas of the skull, skull base, and face, including the orbital (eye) and mandibular (jaw) structures. This deformity most commonly occurs in the posterior aspect of the head (posterior plagiocephaly), resulting in a focal area of flattening on that side and a compensatory prominence, or bulge, on the other side. In addition, the deformity produces anterior displacement of the ear, ear canal, temporomandibular (jaw) joint, forehead and orbital structures on the same side. Cranial deformities may also be classified, inter alia, as brachycephaly (a short, wide head shape), scaphocephaly (a long, narrow head shape), and turricephaly (a pointed head shape).

Non-synostotic posterior plagiocephaly is a very common problem for which parents seek evaluation and recommendations from their family physician or pediatrician. The incidence of this abnormality has increased significantly since publication of recommendations by the American Academy of Pediatrics that neonates (infants) should be put to sleep on their back rather than face down. These recommendations were made to reduce the incidence of Sudden Infant Death Syndrome (SIDS) by eliminating airway and respiratory compromise in the prone (face-down) position, which the Academy considered a possible contributor to the SIDS problem.

Brain growth is responsible for the growth and shaping of the skull, which results from slow, gradual separation of the bones at the cranial sutures. This separation allows for the addition of new bone onto the peripheral edges of the existing bone, producing gradual bone enlargement and reshaping of each bone. As the head enlarges, new bone is added to each bone in an inwardly directed fashion producing an inner surface concave shape to the overall bone. Any force or pressure applied to the exterior surface of the bone will re-direct the growth of bone added to the edges. New bone will be added in a more linear direction, thus reducing the inner surface concavity or producing "flattening" of the bone. Growth of bone does not stop; rather, it is redirected. Therefore, externally applied pressure (e.g., contact with an orthosis) reduces or stops outward growth or migration in that area, and redirects the growth to occur in a direction that is perpendicular to the applied force, which is tangential to the bone surface in that location. Uniform expansion of the remaining bones and sutures, which comprise the cranial vault, is rare. Instead, relative increased growth and expansion of the areas most adjacent to the "flattened" area tends to occur.

Treatment may come in the form of prevention or correction. Regarding prevention, the focus should be to reduce the duration that external pressure is applied to a localized area of the skull. This can be accomplished by moving the same external force to different areas of the skull. This is only achievable by re-positioning the patient's head, which is not possible in a large number of infants (e.g., those having immobility from torticollis). An alternative way to accomplish this is to enlarge the surface area of contact, which reduces the amount of pressure on the specific area, although it still typically results in at least some contact at the area of desired growth. It is also important to restrict the compensatory overgrowth that forms abnormal prominent areas in locations that are perpendicular and adjacent to the area of applied force. This allows for re-direction of growth and expansion in an appropriate normal direction. Devices used for prevention must maintain these properties, but still allow for expected progressive growth.

Prolonged immobility of the head will eventually lead to the development of a positional deformity. The etiology of the immobility may be neurologic/developmental, muscular, skeletal (vertebral) or simply from resting/sleeping preference in the absence of any known cause. Persistent immobility will allow for lateral and posterior deformities to develop.

Despite public knowledge and education regarding the development of these deformities and preventative measures, because infants are usually born with normal head shapes, it appears economically irrational to go through the expense and trouble of obtaining a preventative device if no deformity appears to be present. Development of these deformities is insidious, slowly occurring over weeks and easily overlooked. Frequently, only when the condition is obvious is intervention considered.

Treatment by "repositioning," also called "mobilization"—that is, the act of another person moving the infant's head from side to side at regular intervals—is ineffective for treating or preventing these deformities due to the inherent problems associated with such a method of treatment. Simply put, it is very difficult to keep the child's head in the same position for extended periods of time, as the natural inclination of the child is to revert to his or her preferred sleeping position. Moreover, because "mobilization" is ideally performed every two to three hours, the infant requires constant attention throughout the night, and it is therefore not a practical treatment option. Similarly, children with torticollis cannot be effectively "mobilized" due to the tendency of the head to rotate as a result of involuntary contraction of the neck muscles. In both of these cases, the resulting position of the head—whether by preference or immobility—is most likely not the desired position for correction of deformities and is, as noted above, the cause of deformity in the first place.

To the extent treatment by repositioning might be effective when the above-referenced parameters are satisfied—i.e., a child who does not tend to revert to a preferred sleeping position and is not immobilized due to torticollis, and who can be mobilized regularly every two to three hours—children treated with prevention in this manner still do not obtain a perfectly normal head shape, because the supporting apparatus remains in contact with the skin and conforms the head to an abnormal shape. As a result, forces still act on already-flattened regions of the cranium and inhibit growth at precisely the area of the cranium where growth should be promoted. Due to this ineffectiveness, a large number of these children require additional treatment from five to ten months of age to correct persistent or progressive deformities.

The most common adjuncts available to assist with repositioning are flat- and wedge-shaped foam pads. For example, U.S. Pat. No. 6,473,923 (filed Nov. 22, 2000) (issued Nov. 5, 2002) discloses a body pillow and head positioner attached to a mat. The device is intended to maintain the infant's supine position—i.e., lying on the back, face upward—while reducing the risk of positional plagiocephaly by causing the head to rotate to the side while maintaining the infant's supine position.

One goal for correction of an existing deformity is to eliminate the external forces acting on the flattened area. As with prevention, improved correction can be achieved by providing external forces acting on the compensatory prominent areas of the skull, thereby reducing growth that occurs in these areas and redirecting growth towards a more normal direction and shape. Allowances for growth are also required for correction, but cannot compromise the mechanical ability of a device to correct the existing deformity.

Corrective treatment most often is by application of a custom-made external orthosis, or helmet. See, e.g., Corrective Infant Helmet, U.S. Pat. No. 6,592,536 (filed Jan. 7, 2000) (issued Jul. 15, 2003); Therapeutic and Protective Infant Helmets, U.S. Pat. No. 4,776,324 (filed Apr. 17, 1998) (issued Oct. 11, 1998). Such devices provide an expanded area over the site of the deformity, thereby allowing for correction of the deformity over a three to six month period of time related to brain and skull growth and subsequent reshaping. This prolonged time of use is necessary because of the reduced rate of brain and skull growth during the six- to twelve-month time frame. Due to a decrease in the rate of brain and skull growth to approximately fifty percent of the rate from birth to six months and increased stiffness of bones and cranial sutures, the recommendation is to wear the helmet continuously for twenty-three hours each day for up to twelve months. But despite extended use of these helmets, deformities rarely return to a normal shape. In addition, many health insurance companies and programs refuse to pay for these devices, leaving a large number of infants with no available treatment because of the relatively high cost of the helmets.

Similar to the preventative approaches discussed supra, another proposed approach to correct existing cranial deformities is to soften the material on which the infant's head rests by using a foam pad or memory foam pillow. This method allows the redistribution of inwardly directed forces, but fails to adequately correct cranial deformities because the softened material conforms to the already-abnormal head shape. Specifically, the material still contacts, and therefore applies forces to, the already flattened areas of the head and reduces forces that should be applied at the abnormal cranial bulges. Preventing cranial deformities with this approach is also ineffective because forces continue to act directly on a focused area of the head rather than the entire cranial vault. Because these pads and pillows are not shaped like a normal infant cranium, but are generally flat, forces acting on the cranium from these devices result in cranial flattening, and therefore an abnormal head shape, because the head conforms to the shape of the material (i.e., flat) at the point of contact.

Still another approach is to suspend the infant's head on a flexible material, which, for example, may be a net with an open weave that keeps the infant's head slightly elevated over the resting surface. See Method and Apparatus to Prevent Positional Plagiocephaly in Infants, U.S. Pat. No. 6,052,849 (filed Mar. 18, 1999) (issued Apr. 25, 2000). Although the use of an elastic stretchable material or netting may be slightly better than regular foam for preventing the development of flattened areas, these devices also do not effectively promote normal shaping due to the continuous application of external forces directed at the posterior aspect of the infant's head. In the case of correction, the flexible material will still conform to the already-abnormal head shape and exert forces on the flattened areas. In the case of prevention, the weight of the cranium on the flexible material will tend to immobilize the cranium, which results in prolonged contact of non-uniform forces around the cranium and, again, is precisely the wrong methodology for maintaining an already normal cranial shape. As with the "softened material" approach previously described, forces acting on a smaller area of the head results in reduced cranial growth and expansion because the head conforms to the shape of the material, thus resulting in an abnormal head shape in which the frontal areas are wider than the posterior aspect of the head because the material is applied only to the posterior aspect of the cranium, with the application of constricting forces.

After ten to twelve months of age, little, if any, correction of a cranial deformity can be accomplished with non-operative treatment because of reduced velocity of brain and skull growth, increased thickness of bone, and reduced flexibility of the cranial sutures. Surgical intervention is typically the only effective treatment for moderate to severe deformities in children over twelve months of age.

Alternative methods for correcting this condition without the use of a helmet do not directly address the cause of the problem, and therefore do not effectively treat the condition. All other products and devices, including foam, elastic (and therefore flexible) material or netting, merely distribute or disperse forces over a focused area of the head Because these products and devices remain in continuous contact with the skin, they conform the cranium to the abnormal shape, including the abnormally flattened areas. Thus, the prior art does not remove or eliminate the external forces at flattened areas of the cranium, but rather maintains an abnormal cranial shape and promotes a static deformity.

Finally, attempts to prevent and correct such deformities with the use of headrests also exist. With the exception of the present invention and U.S. Pat. No. 4,825,487 (issued May 2, 1989) to Eberl (hereinafter "Eberl"), the existing headrests are "low profile" devices, which extend only a maximum of 35 mm anterior of the most posterior position of contact with the infant's skull (about 30% or less of the anterior-posterior distance) and only contact the very or most posterior area of the head. See, e.g., WO 2006/102407 (published Sep. 28, 2006); European Patent No. EP 1 665 958 (filed Aug. 25, 2004); New Zealand Patent No. 510,421 (filed Mar. 8, 2001). However, the low profile (i.e., posterior only) headrests are ineffective based on bio-mechanics of such devices, as lateral support is necessary in order to achieve effective prevention and treatment These available and proposed low-profile devices provide insufficient support and positioning to overcome the problem of immobility leading to development and progression of positional deformities. These deformities develop despite any differences or modifications in shape, size, or consistency—that is, prevention or any level of correction with low profile devices will require turning of the head, and any prevention or correction achieved would be due to "repositioning" treatment as described supra, thus making the device unnecessary. The treatment provided in this situation is repositioning, not the low profile device. And as noted above, the ability to reposition or turn the head is a luxury and is not possible in a large number of instances. Lateral support, however, allows one to overcome the problem of immobility, which is not achievable with a low-profile device.

While Eberl would not be considered a "low profile device" as discussed supra, it also provides insufficient lateral support. As shown in FIG. 4 and FIG. 5 of Eberl, the sidewalls are outwardly angled from the longitudinal axis of the device, which inherently means Eberl provides no immediately adjacent lateral support when the infant's cranium is rotated in either direction. In this manner, Eberl is effectively the same as the low-profile devices, but with an added disadvantage that the Eberl sidewalls are excessively high such that a very young infant placed on the Eberl invention is susceptible to the development of obstructive amblyopia due to the obstruction of the visual field/pathway. In addition, Eberl is made from soft, conforming material, which, as noted with respect to foam mattresses and pads, conforms to an abnormal head shape.

Currently there is no specific apparatus available to provide effective corrective and preventative treatment for non-synostotic cranial deformities in the age range of birth to five months. To avoid the difficulties and pitfalls associated with currently available devices aimed at treating non-synostotic cranial deformities, the present invention discloses a corrective headrest for use at the very first recognition of development of a deformity. The headrest and method allow effective treatment during the rapid period of brain and skull growth (birth to six months), thereby providing rapid correction of the deformity. Children with predisposing conditions may require prolonged treatment. Early effective treatment is the key to providing complete correction of these deformities.

BRIEF SUMMARY OF THE INVENTION

The present invention discloses, inter alia, a device and method for correcting and/or preventing an infant's abnormally-shaped cranium by applying external forces over time with the growth of an infant to achieve normal shaping of the infant's head. Unlike the prior art, the present invention both 1) prevents abnormal shaping of an infant's cranium by causing even growth of the infant's normally shaped head and 2) provides forces that act unevenly across an abnormally shaped cranium to correct existing cranial deformities. The embodiments of the present invention include a solid, one-piece headrest structure of uniform consistency, having a depression that is molded to approximate the posterior and side aspects of the skull and head, with cervical, or neck, support. The material that contacts the infant's cranium is semi-rigid and relatively non-flexible, maintains its overall shape under stress, and demonstrates minimal superficial focal elasticity only at the site of cutaneous contact. In the preferred embodiment, the hardness of the material the contacts the infant's cranium is between 65 and 75 (inclusive) on a OO durometer scale.

To correct existing cranial deformities, the present invention applies inwardly-directed external forces only to areas of bony prominence and minimizes (or altogether eliminates) these forces on the areas of the skull that are less prominent (or flattened). The present invention is non-conforming to the shape of an abnormal skull. The forces exerted allow for accelerated expansion of the skull in the less prominent (flattened) areas coincident with brain and skull growth, allowing for return to a normal symmetric cranial shape.

In addition, the headrest prevents development of abnormal cranial shaping by providing a round, normally-shaped contour for contact with the posterior and side aspects of the head, even if the head is turned slightly to one side or the other. Moreover, because the surface is semi-rigid, the surface will allow for even cranial growth over this area of contact, thereby maintaining the infant's normal head shape.

The preferred embodiment of the present invention is made from an impermeable high-density foam, which provides ease of cleaning as well as flame retardant properties. Other embodiments of the present invention are made from other foam variants, including open cell foam covered with a vinyl or other coating or closed cell foam layered over or applied to more rigid solid or hollow plastic (e.g., PVC or nylon).

Therefore, in accordance with one aspect of the present invention, a headrest having a semi-rigid body for correcting the shape of an infant's abnormally-shaped cranium includes a bottom surface for contact with a resting surface; a top surface for contact with the cranium of the infant; a generally hemi-ellipsoidal depression in the top surface; and a ridge at one end of the depression for supporting the neck of the infant. The shape of the depression corresponds to the shape of a normal infantile cranium. The top surface provides external forces acting on abnormal cranial bulges of the infant's cranium and eliminates external forces that act on abnormal cranial depressions of the infant's cranium.

Other features of the headrest include a rim that defines a substantial portion of the depression, as well as the headrest having a side surface between the bottom surface and the top surface. Furthermore, an additional feature of the headrest includes a curved front surface that cradles the shoulders and further supports the neck of the infant.

According to another feature of the present invention, antero-lateral support provided by the present invention is clearly innovative in its ability to provide treatment from birth to ten months of age while not requiring any enlargement, change, or modification during this period of time. Specifically, according to this feature of the invention, lateral support is provided in conjunction with an anatomically correct shape. Elevated lateral support surfaces allow for continued growth from birth to approximately ten months of age while maintaining or producing a normal head shape, and no change, modification, or enlargement is required for approximately the first year. Because of the lateral support surfaces, the present invention is not only able to correct deformities, but also prevents them from occurring.

BRIEF DESCRIPTION OF THE SEVERAL VIEWS OF THE DRAWINGS

FIG. 9A and FIG. 9B show infant craniums of approximately 36.5 and 46.5 cm in circumference, respectively, positioned in the preferred embodiment.

FIG. 10 is a partial sectional view of the preferred embodiment of the present invention with an infant having a normally shaped cranium is positioned on the contact surface of the headrest.

FIG. 16 is a partial sectional view of the headrest through the inclined first plane of FIG. 10 wherein the plagiocephalic cranium is rotated thirty degrees clockwise about its longitudinal axis to contact a lateral support surface thereof.

FIG. 17 is a partial sectional view of the headrest through the inclined first plane of FIG. 10 in use with a brachycephalic cranium.

FIG. 18 is a partial sectional view of the headrest through the inclined first plane of FIG. 10 wherein the brachycephalic cranium is rotated forty-five degrees clockwise about its longitudinal axis to contact a lateral support surface thereof.

DETAILED DESCRIPTION OF THE INVENTION

Figure 1:
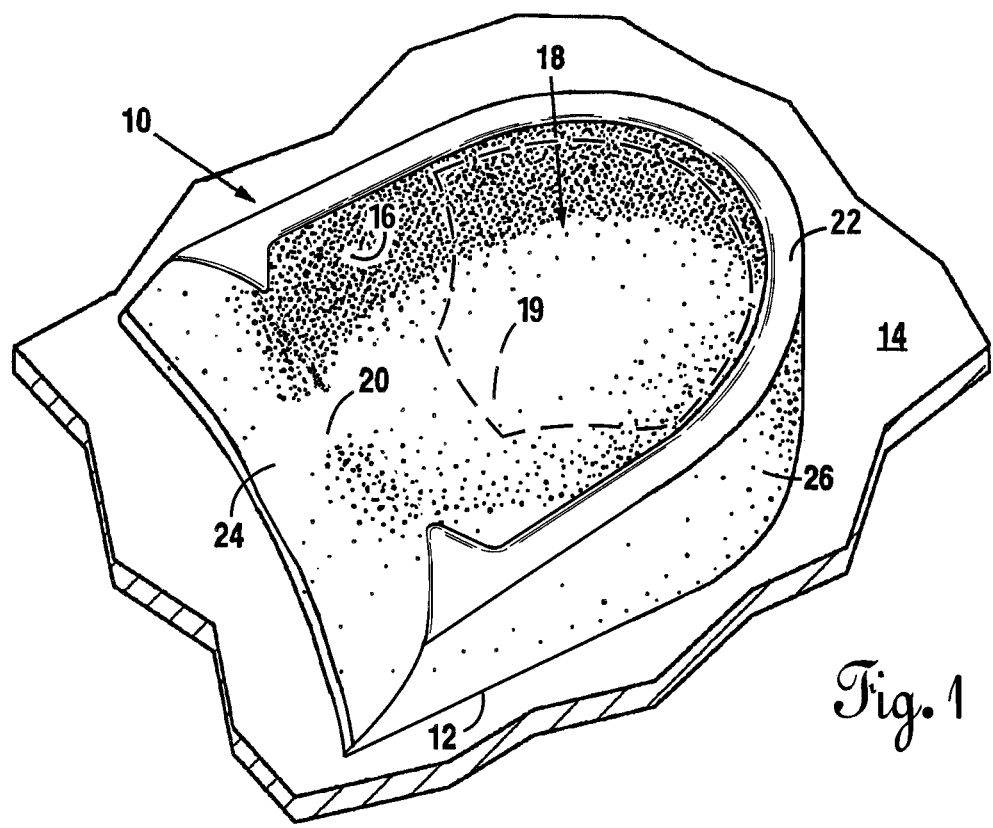
FIG. 1 is a perspective view of the preferred embodiment of the present invention.
Figure 2:
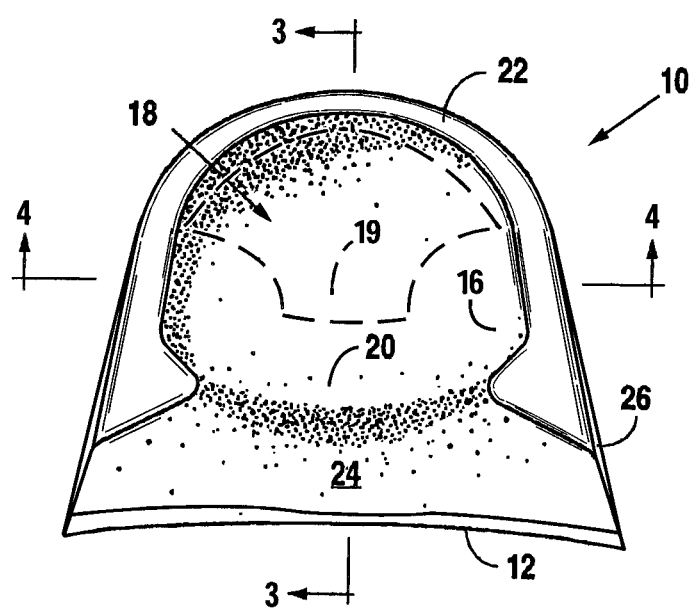
FIG. 2 is a frontal view of the preferred embodiment of the present invention.

When referencing the figures, standard anatomical terms of location are used. For example, a sagittal plane is a plane parallel to the sagittal suture 5 and divides the body into sinister and dexter portions. A coronal plane divides the body into posterior and anterior portions. A transverse plane divides the body into superior and inferior portions.

FIG. 1 through FIG. 4 show a headrest 10 that is the preferred embodiment of the present invention. The headrest 10 comprises a bottom surface 12 for contacting a resting surface 14, and a top surface 16 for contacting an infant's cranium. The top surface 16 comprises a generally hemi-ellipsoidal depression 18, a contact surface 19 that corresponds to the shape of a normal infantile cranium, and a rim 22 defining a substantial portion of the depression 18. At one end of the depression 18, a ridge 20 is positioned to support the neck of the infant. The top surface 16 is preferably made of a closed cell foam material, but may alternatively be made of open cell foam material covered with a vinyl or other surface coating, closed cell foam layered over higher density foam, open cell foam layered over higher density foam, or closed cell foam layered over a more rigid solid or hollow plastic.

A front surface 24, preferably curved, is positioned to cradle the infant's shoulders and support the neck of the infant while the infant's cranium is in contact with the top surface 16. A preferably-curved side surface 26 extends between the rim 22 and the bottom surface 12. In this preferred embodiment, the headrest 10 is a continuous, uniform, solid body. However, it is anticipated that variations of the uniformity or continuity of the body could occur and be utilized.

In normal operation for correction of an abnormally shaped infant cranium, the headrest 10 is placed on the resting surface 14 so that the bottom surface 12 is in contact therewith. The infant's head is then placed in the depression 18 with the infant's cranium resting on the contact surface 19. Initially, the posterior and part of the side aspects of the infant's head contact the contact surface 19, although during the sleep period the infant's head may roll to one side or the other. Throughout the sleep period, the infant's neck is supported by the ridge 20. The infant's shoulders are aligned in and cradled by the curved front surface 24. As the infant's head makes contact with the top surface 16, the contact surface 19 provides external forces acting on any abnormal bulges of the infant's cranium and reduces or eliminates external forces that act on abnormal depressions (flattened areas) of the infant's cranium. This contact reduces the net outward forces from brain and skull growth at these prominences, and redirects the growth to areas of the cranium where the infant's head is not in contact with the top surface 16.

It should be noted that that amount of contact of the infant's cranium with the contact surface 19 varies according to the size of the infant's cranium. For example, a newborn infant's cranium will contact relatively little of the contact surface 19 and, in a non-rotated position, the contact will occur primarily at the occipital bone and adjacent areas of the left and right parietal bones. As the infant grows over time, the size of the cranium approaches the size of the depression 18, with an increasingly greater area of contact.

The headrest 10 works similarly to prevent cranial deformities. The infant's head is placed in the depression 18, the contact surface 19 of which matches the round, normally-shaped contour of the posterior and side aspects of the head, resulting in the head "growing into" the properly-shaped contact surface 19 over time. As the cranium grows, any existing deformities will conform to the normal shape of the contact surface 19 of the depression 18. Because of its semi-rigid character, the contact surface 19 allows the infant's cranium to grow evenly and maintain its normal shape. Typically, this occurs as the headrest is used from two to seven months of age, although, due to statistical variations in head circumference of infants, this is more appropriately a function of the cranial circumference (i.e., until the head grows to the same size as the depression 18).

Figure 7A:
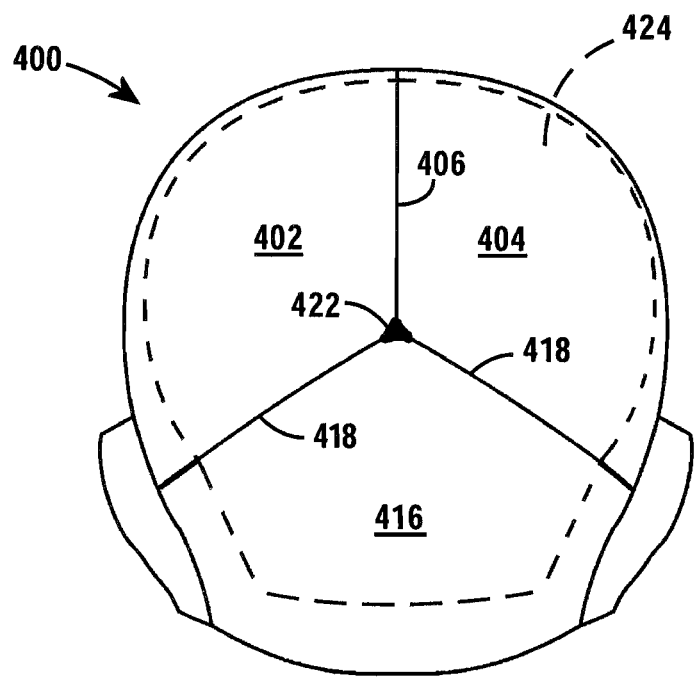
FIG. 7A and FIG. 7B are a rear elevational view and a top elevational view, respectively, of a normally-shaped infant cranium showing the surface area that contacts the headrest when the infant's head is supinely positioned in the orthosis.
Figure 7B:
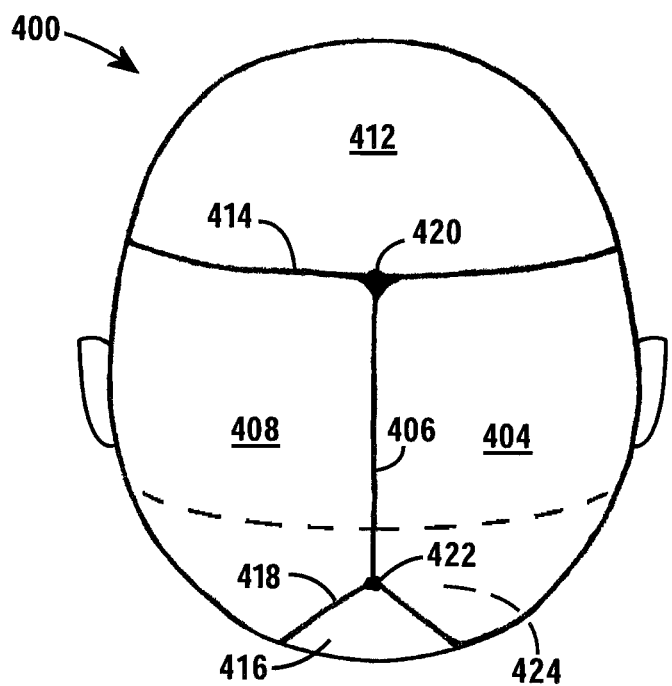

FIG. 7A and FIG. 7B are a rear elevational view and a top elevational view, respectively, of a normally-shaped infant cranium 400 having a circumference of less than 46.5 cm and a left parietal bone 402 connected to a right parietal bone 404 with the sagittal suture 406. The left and right parietal bones 402, 404 are connected to the frontal bone 412 via the coronal suture 414 and to the occipital bone 416 with the lamboidal suture 418. The sagittal suture 406 joins the coronal suture 414 at the anterior fontanelle 420. The lamboidal suture 418 joins the sagittal suture 406 at the posterior fontanelle 422. When positioned in the preferred embodiment of the headrest 10, a cranial surface area 424 that includes a portion of the occipital bone 416, and the posterior portions of the left and right parietal bones 402, 404 makes contact with the contact surface 19 of the depression 18, as described supra.

Figure 8A:
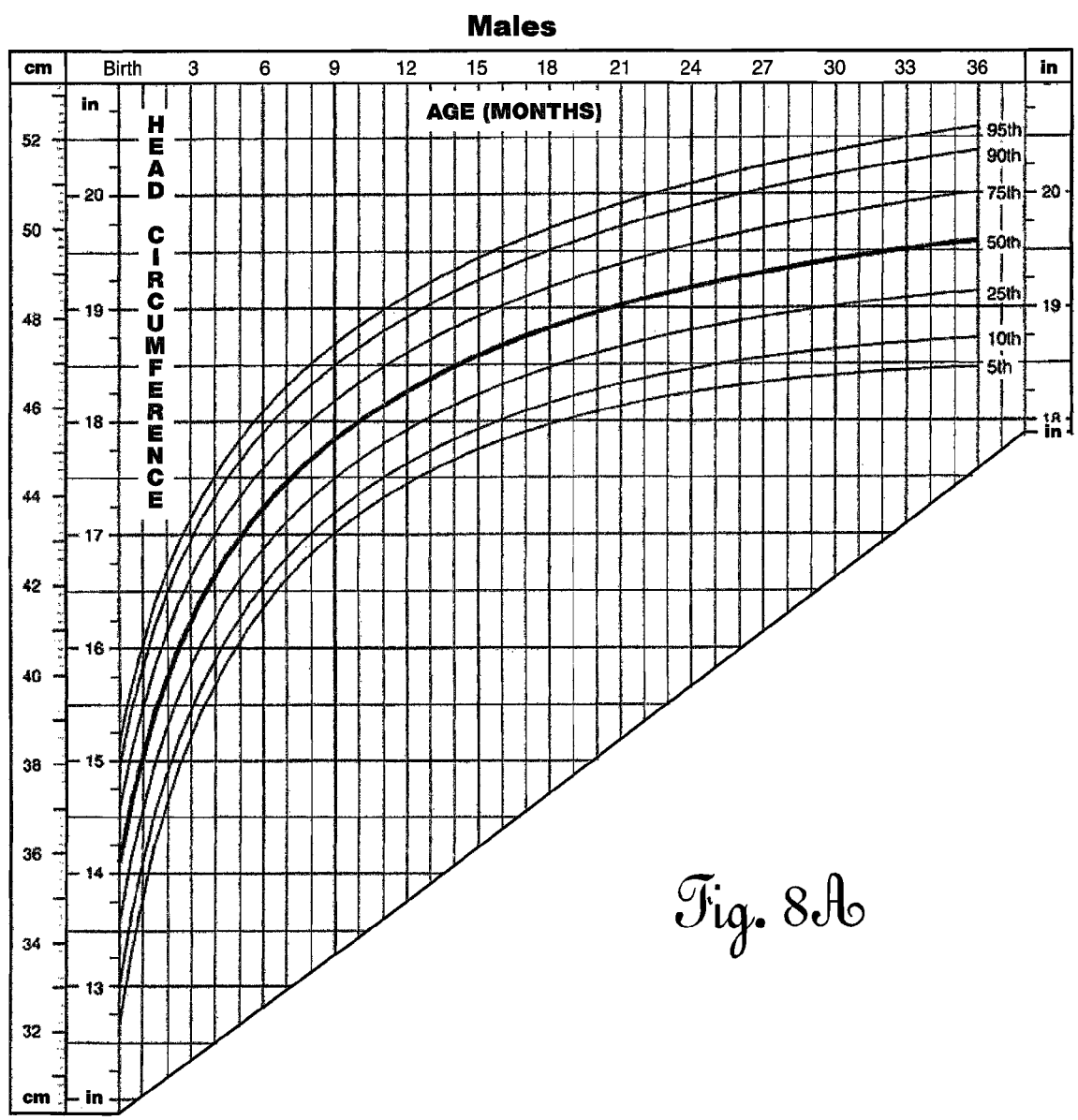
FIG. 8A is a chart showing head circumference-for-age of males from birth to thirty-six months.
Figure 8B:
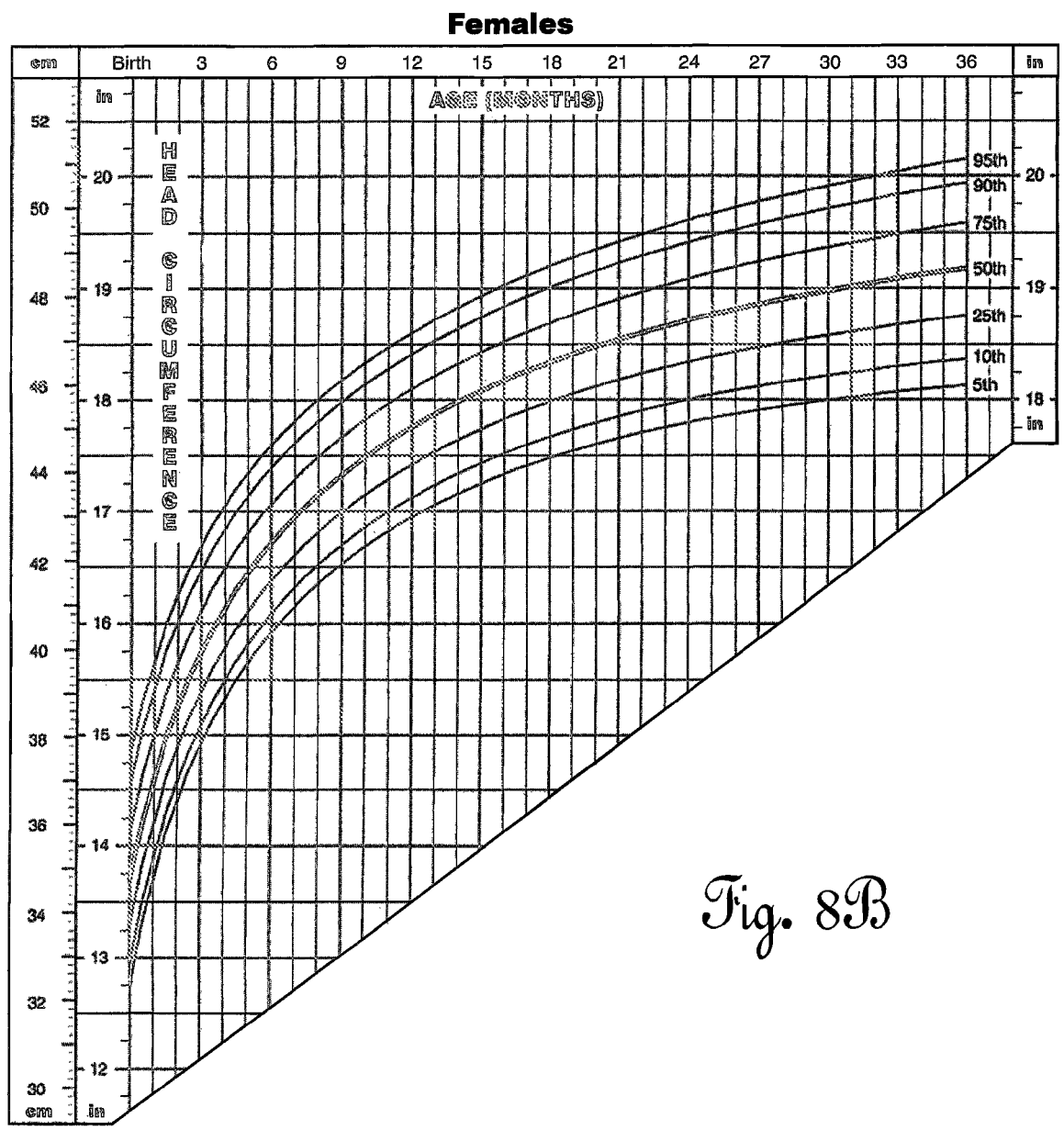
FIG. 8B is a chart showing head circumference-for age for females from birth to thirty six months.

FIG. 8A shows head circumference-for-age of males from birth to thirty-six months. FIG. 8B shows head circumference-for age for females from birth to thirty six months. As can be seen from these figures, less than five-percent of all infants have a head circumference of less than 36.5 cm at two months of age. At seven months, at least ninety-five percent of all infants have a head circumference less than 46.5 cm. Thus, a preferred embodiment of an orthosis having the features of the present invention is configured to address, at a minimum, head circumferences within a range of 36.5 cm to 46.5 cm in circumference. However, it is anticipated that this will accommodate head circumferences within a range from thirty-two (32) to forty-eight (48) centimeters and still provide the benefits described herein.

FIGS. 9A and 9B depict side elevation views of two infants having normally-shaped craniums of differing circumferences positioned in the same preferred embodiment of the cranial orthosis 10, and show the position of predetermined coronal planes relative to the orthosis 10. Head circumference for an infant is the largest distance around the head, and generally is found in a plane 47 that intersects the forehead of the infant and the most posterior point 54 of the cranium.

More specifically, FIG. 9A depicts a first infant's cranium 49 that has a circumference of 46.5 cm, and has an anterior-posterior distance $APD_1$, which is the distance between the most posterior point 54 on the infant's head and the most anterior point 57 on the infant's forehead. A first coronal plane 51 is defined as a coronal (i.e., horizontal) plane positioned approximately at forty percent (40%) of the anterior-posterior distance $APD_1$, a position which approximates the height of the earhole 52 for an infant having this head size. With respect to the orthosis 10, the first coronal plane 51 is positioned approximately 6.2 to 6.7 cm above the nadir 23 (i.e., lowest point) of the depression 18. A third coronal plane 21 is defined as a coronal plane positioned at the most anterior contact point 27 between the infant's cranium 49 and the headrest 10. With respect to the headrest 10, the third coronal plane 21 is positioned approximately 8.0 to 8.6 cm from the bottom surface. Similarly, FIG. 9B depicts a second infant cranium 55 of 36.5 cm in circumference. A second coronal plane 56 is defined as a coronal plane positioned at approximately seventy percent (70%) of $APD_2$ for an infant having this head size. With respect to the orthosis 10, the second coronal plane is positioned approximately 8.8 to 9.3 cm above the nadir 23 of the depression.

Figure 3:
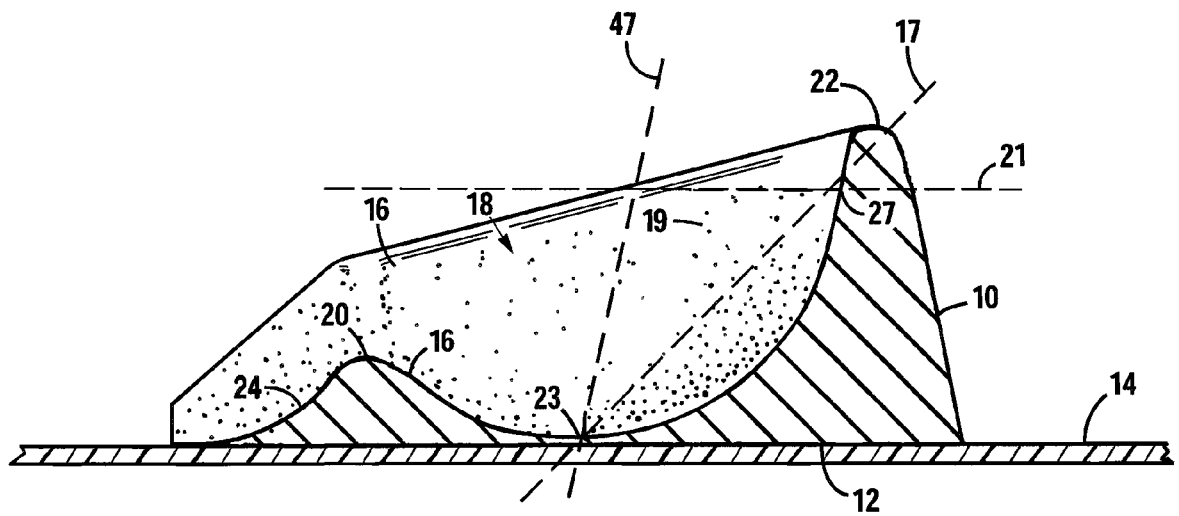
FIG. 3 is a sectional view of the craniocervical orthosis along Line 3-3 of FIG. 2.
Figure 4:
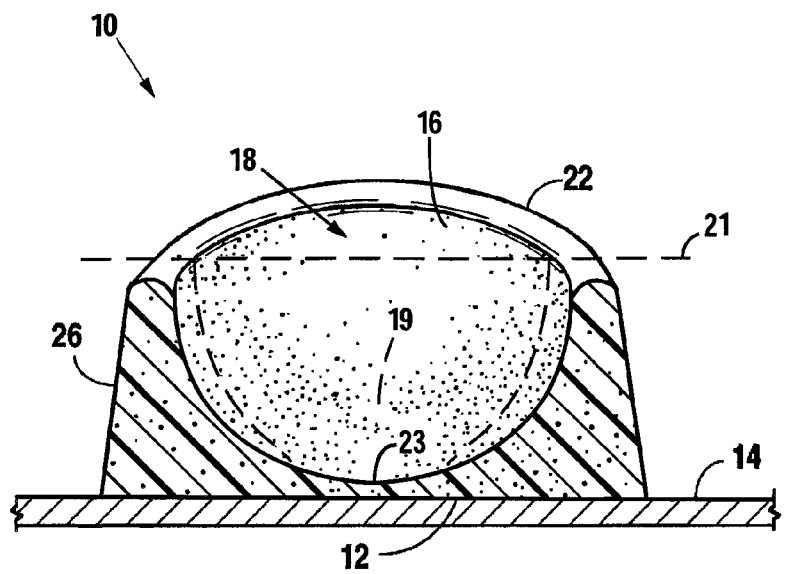
FIG. 4 is a sectional view along Line 4-4 of FIG. 2.

As shown in FIG. 3, in the preferred embodiment, the contact surface 19 is defined as the surface area of the depression 18 that is (1) superior to an inclined first plane 47 angled between 10 and 20 degrees from vertical in the superior direction and intersecting the nadir 23, and (2) posterior of the third coronal plane 21. At a minimum, however, the contact surface 19 is at least the surface area of the depression 18 that is (1) superior to a diagonal plane angled 45-degrees from vertical in the superior direction and intersecting the nadir 23, and (2) posterior of the third coronal plane 21.

Figure 5:
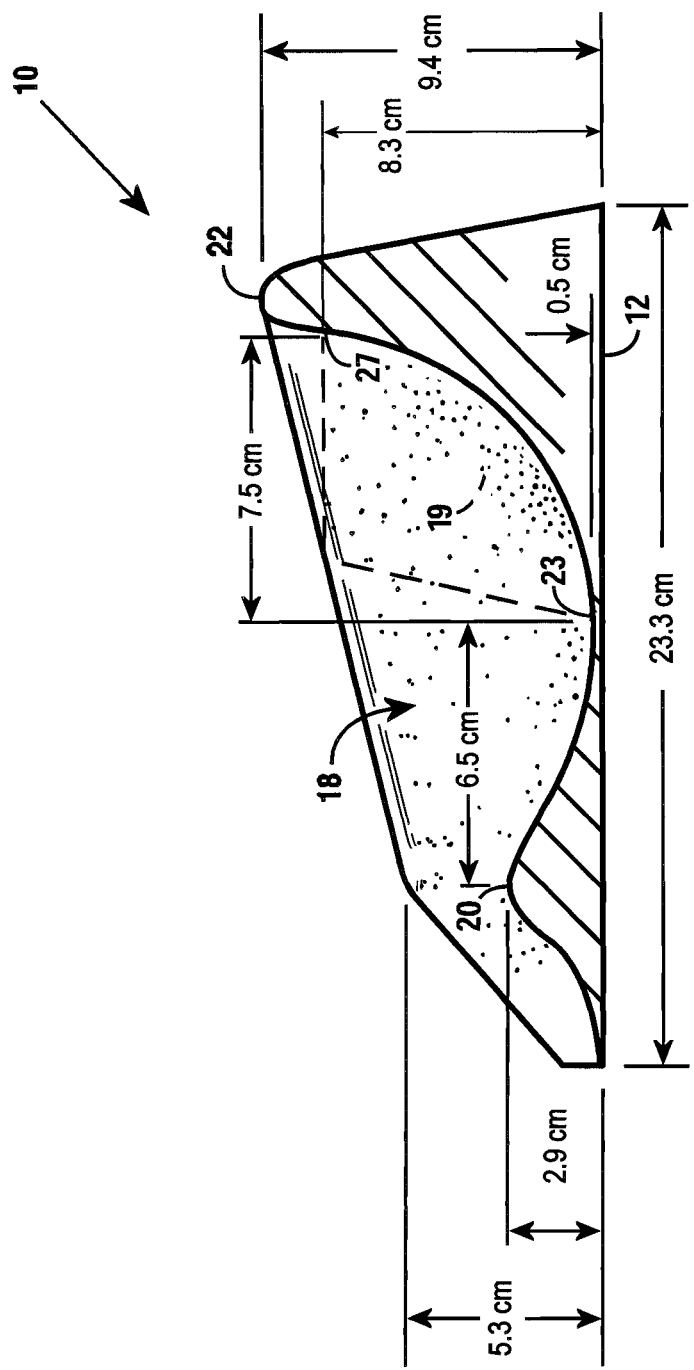
FIG. 5 and FIG. 6 depict dimensions of a preferred embodiment of the orthosis.
Figure 6:
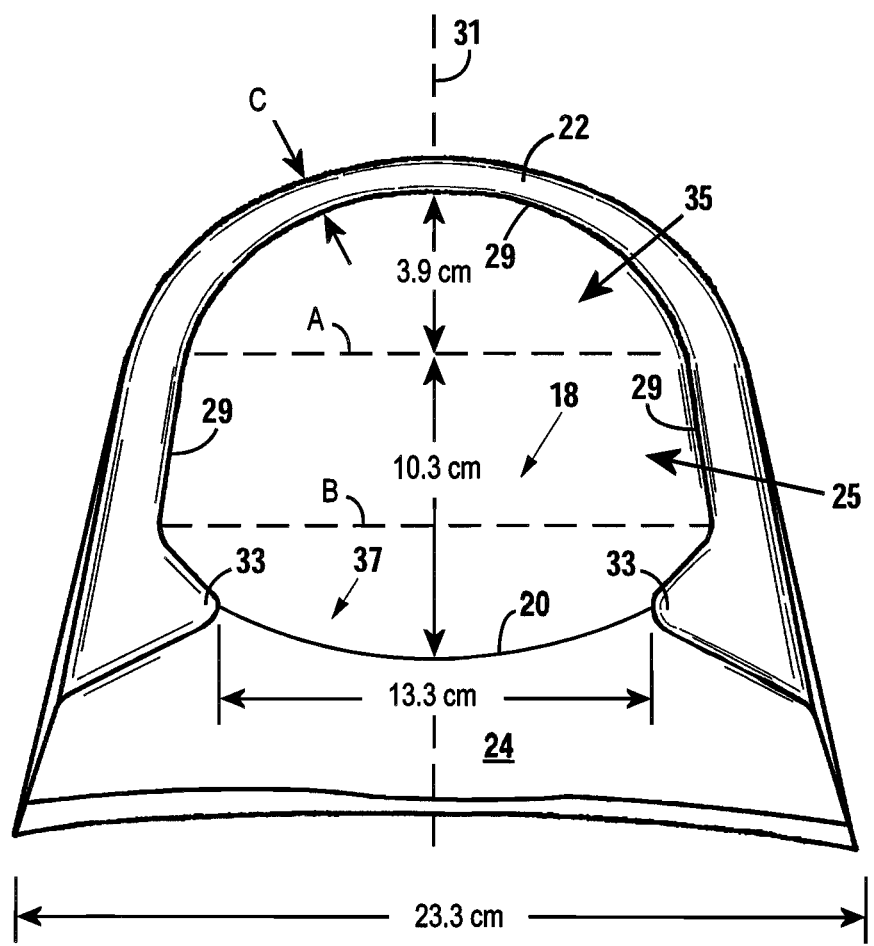

FIG. 5 and FIG. 6 depict preferred dimensions of a specific embodiment of the orthosis 10. As shown, the length of the orthosis 10 from its most inferior to its most superior point is 23.3 cm. The height of the ridge 20 above the bottom surface 12 where it intersects the longitudinal axis is 2.9 cm. At its highest point, the rim 22 is 9.4 cm from the bottom surface 12. The ridge 20 is 6.5 cm from the mid-cranial transverse plane 70, which is the transverse plane intersecting the nadir 23 of the depression 18. The mid-cranial transverse plane is 7.5 cm from the most superior contact point 27. In the preferred embodiment, that superior point 27 is 8.3 cm from the bottom surface 12.

In the preferred embodiment, as shown in FIG. 6, in which the shading has been removed for clarity, the width of the curved front surface 24 is 23.3 cm and the width of the ridge 20 is 13.3 cm. The depression has a front portion 37 extending 2.3 cm from the ridge 20 along the horizontal, longitudinal axis 31, and is bounded on either side with symmetrical protrusions 33. A middle portion 25 is immediately adjacent the front portion 37 wherein the interior boundary 29 of the rim 22 adjacent the middle portion 25 is substantially straight.

An arced rear portion 35 is adjacent the middle portion 25, wherein the interior boundary 29 of the rim is symmetrically curved to connect one sides of the middle portion 25 to the other. The maximum depth of the arced rear portion 35 from the middle portion 25 to the interior boundary 29 of the rim 22 along the horizontal longitudinal axis 31 is 3.9 cm. The greatest width of the middle portion 25 is at the boundary with the front portion 37 (line B) at 16.3 cm. The middle portion 25 is narrowest immediately adjacent the arced rear portion 35 (line A) at 12.7 cm. The depth of the middle portion 25—i.e., the distance between the front portion 37 and arced rear portion 35—is approximately 8.0 cm. The superior- to inferior widening of the middle portion 25 provides space for the ears of an infant who is resting in the headrest 10 in a supine position, which is important to avoid misshaping of the ear. The depth of the depression 18 from the crest of the ridge 20 to the interior boundary of the rim 22 along the horizontal longitudinal axis is 14.2 cm. The thickness C of the rim 22 around the arced portion 35 is approximately 2 cm. Although the dimensions of the preferred embodiment are given with specific measurements, it is understood that the measurements could vary slightly without altering the effectiveness of the device. In that regard, the dimensions provided are understood to be substantial approximations of the preferred embodiment of the device.

Figure 11:
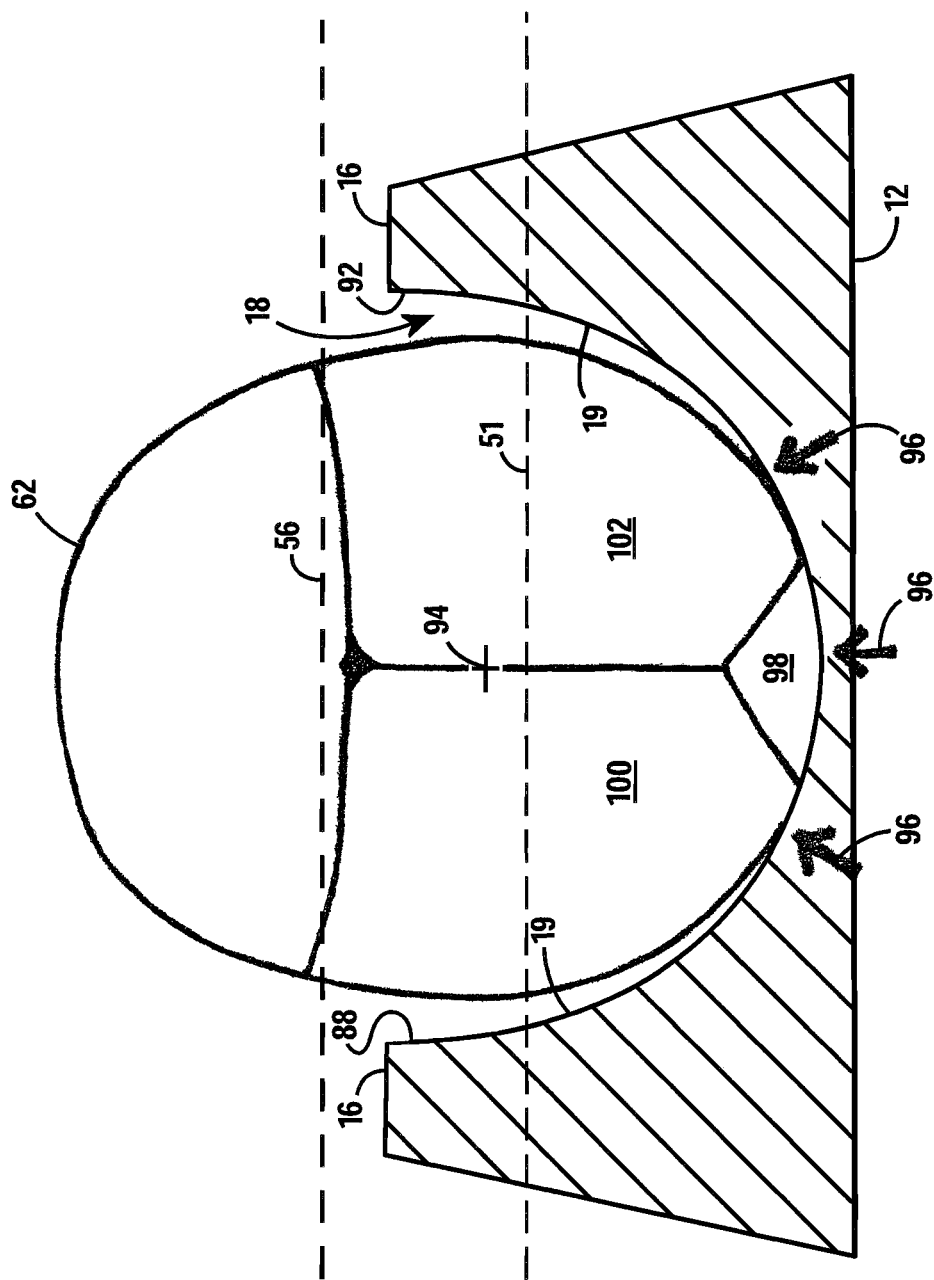
FIG. 11 is a partial sectional view of the headrest through the inclined first plane of FIG. 10.

Returning now to a description of the present invention, FIGS. 10 and 11 depict the preferred embodiment of the present invention in which an infant 60 having a normally-shaped cranium 62 of approximately forty (40) centimeters in circumference is supinely positioned on the headrest 10. The first coronal plane 51—as defined above with respect to the predetermined circumference of 46.5 cm—extends longitudinally, and is parallel to the second coronal plane 56. The mid-cranial transverse plane 70 is orientated perpendicular to the first coronal plane 51 and extends through the nadir 23, in which the most posterior point 54 of the cranium 62 rests. An inclined first plane 74, which is representative of a typical plane in which the head circumference is measured, is positioned superior and inclined relative to the mid-cranial transverse plane 70, and intersects the nadir 23, and the most anterior point on the forehead.

As noted with respect to FIG. 1 through FIG. 4, the headrest 10 (or orthosis) comprises the bottom surface 12 that contacts the resting surface 14 during use and a contact surface 92 that contacts the infant's cranium 62. The generally hemi-ellipsoidal depression 18 is formed in the top surface 16 with at least a contact surface 19 (see FIG. 3) having a shape of a portion of a normal infant cranium 62. In the preferred embodiment, and as noted with respect to FIG. 3 supra, the contact surface 19 has a surface area generally corresponding to the posterior aspects of the left and right parietal bones in addition to a substantial portion of the occipital area, as discussed with reference to FIG. 5. The top surface 16 is semi-rigid and relatively non-flexible, maintains its overall shape under stress, and demonstrates minimal superficial focal elasticity at the site of cutaneous contact. The ridge 20 at an end of the depression 18 supports, and is contoured to the shape of, the infant's neck 86.

At least the contact surface 19 of the preferred embodiment has a hardness of between sixty-five and seventy-five when measured with a OO-scale durometer, which is the preferred hardness required for the both prevention and correction of positional deformities as described herein. However, because the headrest 10 is preferably of uniform consistency, it is anticipated that the entire outer surface of the headrest 10 will have the same hardness. It should be noted that prevention only, as opposed to both prevention and correction, can be accomplished with a hardness of between twenty-five and thirty-five on the same scale.

Still referring to FIG. 10 and FIG. 11, the contact surface 19 further comprises at least a portion of first and second lateral support surfaces 88, 92. A portion 90 of the first and second lateral support surfaces 88, 92 is positioned anterior of the first coronal plane 51 and superior to the mid-cranial transverse plane 70. In order to prevent obstructive amblyopia, the first and second lateral support surfaces 88, 92 do not extend anteriorly of the second coronal plane 56, as providing a completely unobstructed visual field is imperative to eliminate the risk of iatrogenic-induced neuro-opthalmological injury (i.e., obstructive amblyopia).

FIG. 11 is a partial sectional view of the normal infant cranium 62 in the inclined first plane 74 of FIG. 10. In the preferred embodiment, the first and second lateral support surfaces 88, 92 are substantially vertical at their upper end with slight curvature anterior of the first coronal plane 51. When the infant's cranium 62 is in the supine position, contacting forces 96 are applied proximal to the occipital bone 98 at the posterior aspect of the cranium 62 with only minimal application at the most posterior end of the parietal bones 100, 102. As growth occurs, the left and right parietal bones 100, 102 expand laterally and eventually contact substantially the entire contact surface 19 when the infant's cranium 62 grows to a circumferences of 46.5 cm as shown in FIG. 9A. In this manner the shape of the parietal and occipital regions on the infant's cranium 62 conforms over time (i.e., months) to the shape of the contact surface 19.

Figure 12:
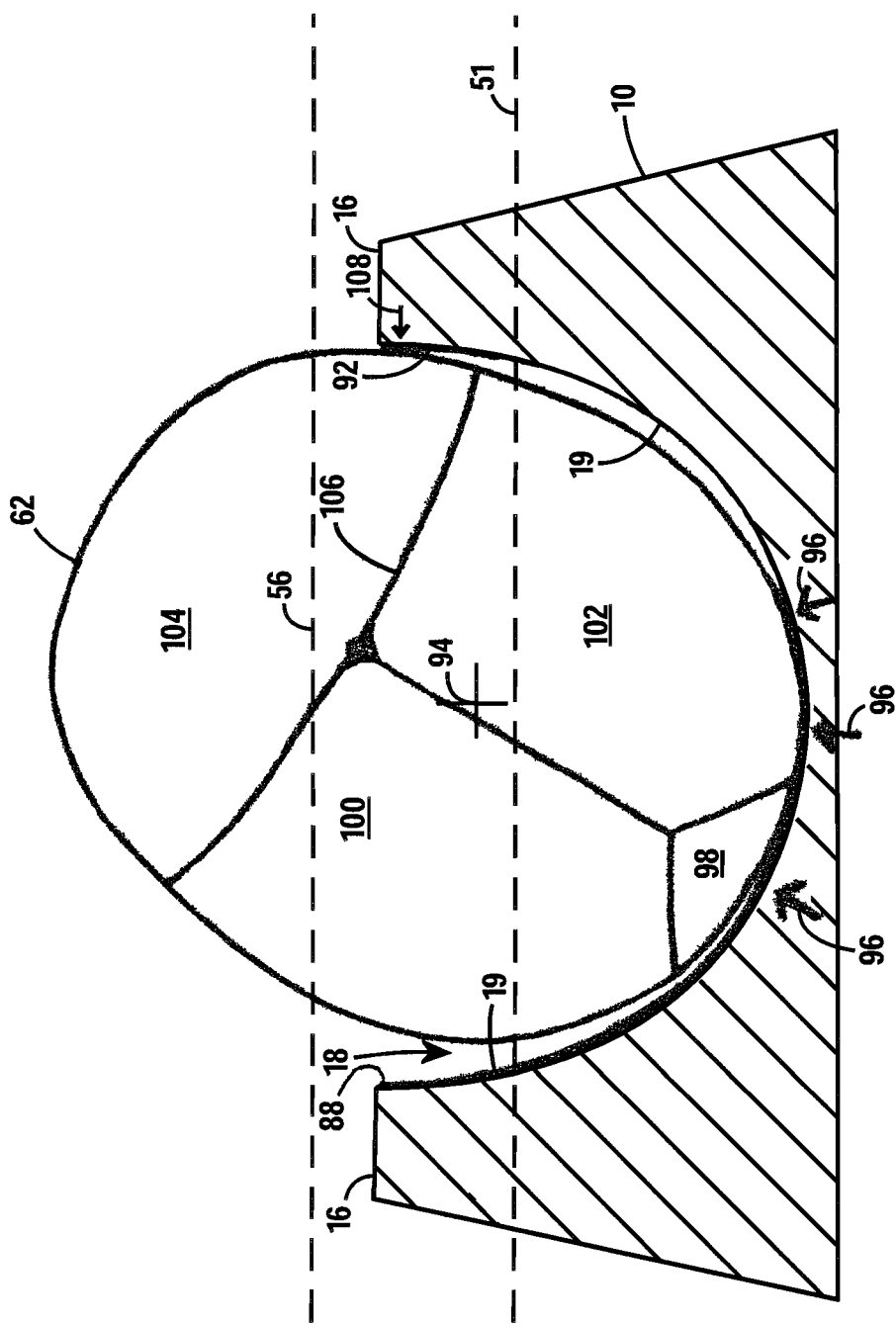
FIG. 12 is a partial sectional view of the headrest through the inclined first plane of FIG. 10 wherein the normal infant cranium is rotated thirty degrees clockwise about its longitudinal axis to contact a lateral support surface thereof.

FIG. 12 depicts the normal infant cranium 62 shown in FIG. 11 rotated thirty degrees clockwise about the longitudinal axis 94. Such rotation causes a corresponding shift in the area of contact of the cranium 62 with the contact surface 19, and thus where external forces 96 are applied to the cranium 62. The contact forces 96 still contact the occipital bone 98 and a greater portion of the posterior right parietal bone 102. In addition, the second lateral support surface 92 contacts the cranium 62 at the frontal bone 104 anterior of the coronal suture 106.

As overall growth of the cranium 62 occurs, less rotation of the cranium 62 is allowed, which results in further maintenance of the normal head shape. Additional expansion and overall growth causes eventual de-rotation of the cranium 62 back to twenty degrees of rotation or less with the contact surface 19 and first and second lateral support surfaces 88, 92 limiting lateral expansion of the parietal bones 100, 102. In other words, as the infant continues to grow and the circumference of the cranium 62 approaches the size of the depression 18, the head is progressively limited to less rotation, resulting in the head "growing into" the properly-shaped contact surface 19. For example, if the size of the cranium 62 is identical to the size of the depression 18, rotation of the cranium 62 will be entirely prohibited. Thus, as the cranium 62 grows, any existing deformities will conform to the normal shape of the contact surface 19 of the depression 18.

Figure 13:
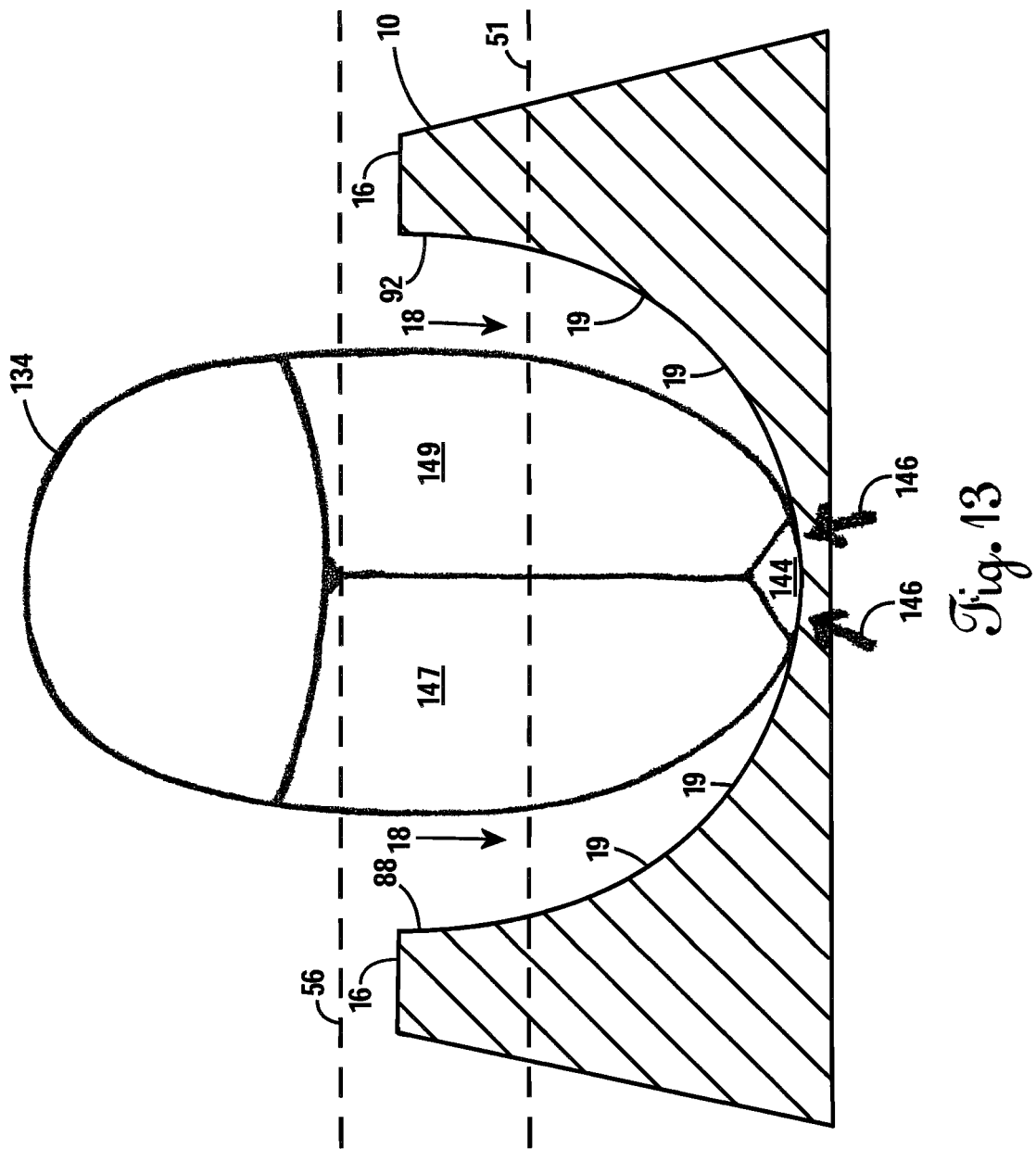
FIG. 13 is a partial sectional view of the orthosis through the first plane of FIG. 10 of a scaphocephalic cranium.

FIG. 13 depicts a partial sectional view of the inclined first plane 74 in FIG. 10 wherein a scaphocephalic cranium 134 of an infant is supinely positioned in the depression 18 in the top surface 16 of the orthosis 10. In this supine position, the contact surface 19 of the depression 18 causes forces 146 to act on the scaphocephalic cranium 134 at the occipital bone 144. If this non-rotated, supine position can be maintained, the absence of forces acting on the parietal bones 147, 149 will allow the parietal bones 147, 149 to grow laterally into a normally-shaped cranium.

Figure 14:
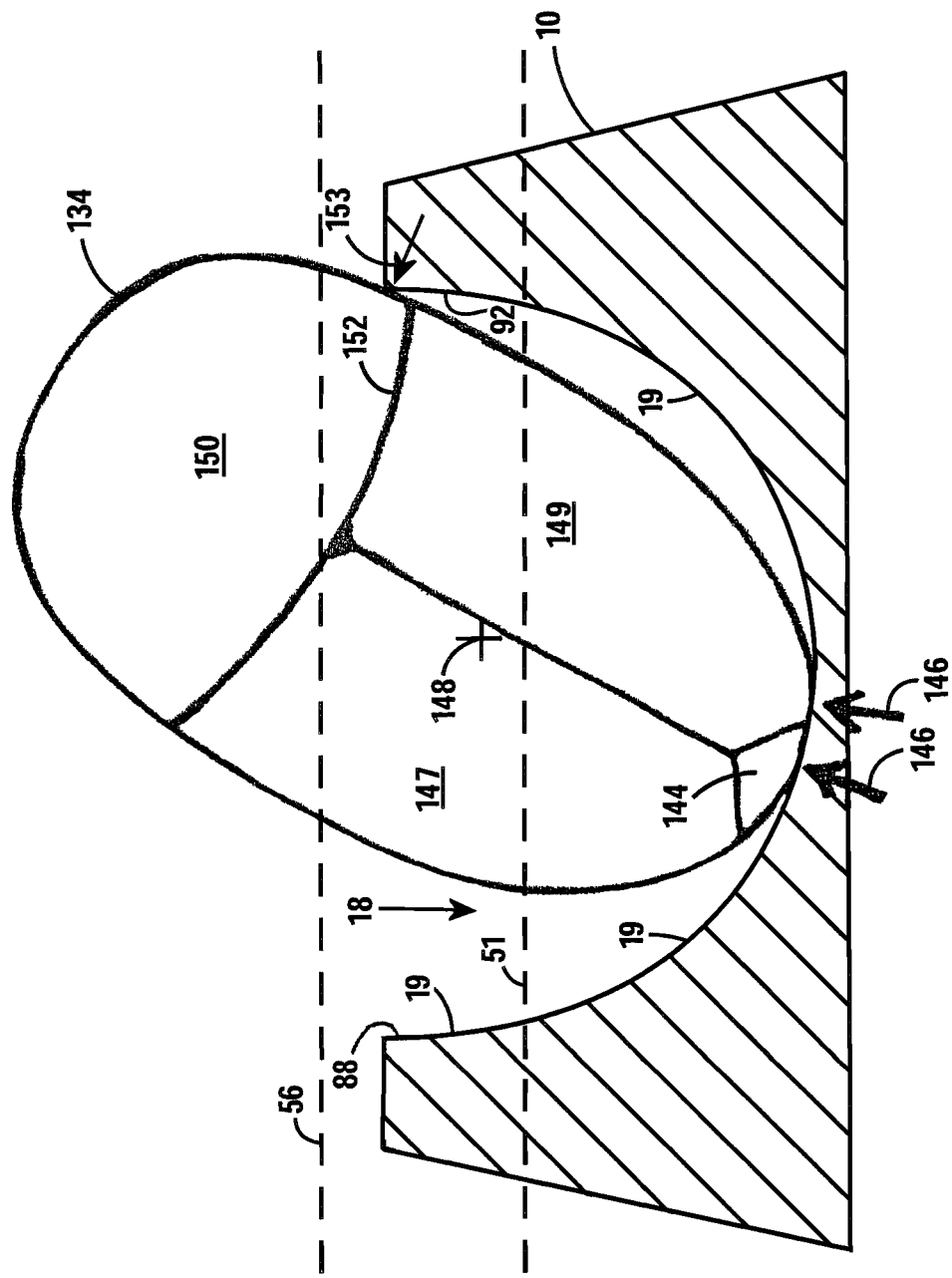
FIG. 14 is a partial sectional view of the headrest through the first plane of FIG. 10 wherein the scaphocephalic cranium is rotated thirty degrees clockwise about its longitudinal axis to contact a lateral support surface thereof.

FIG. 14 depicts the scaphocephalic cranium 134 shown in FIG. 11 rotated thirty degrees clockwise about its longitudinal axis 148. In this rotated position, the second lateral support surface 92 contacts the frontal bone 150 and thereby prevents contact between the mid- or upper-right parietal bone 149 with the contact surface 19 of the depression 18, and allowing for only minimal contact with the right parietal bone 149 at its most posterior point. Once again, the contact surface 19 of the depression 18 contacts and provides forces acting on the occipital bone 144. The absence of contact and forces 146 acting on the left parietal bone 147 and almost all of the right parietal bone 149 allows for parietal expansion and progression toward a normal head shape. Rotation in the counter-clockwise direction results in similar contact of the cranium 134 with the orthosis 10 on the opposite side of the cranium 134.

Figure 15:
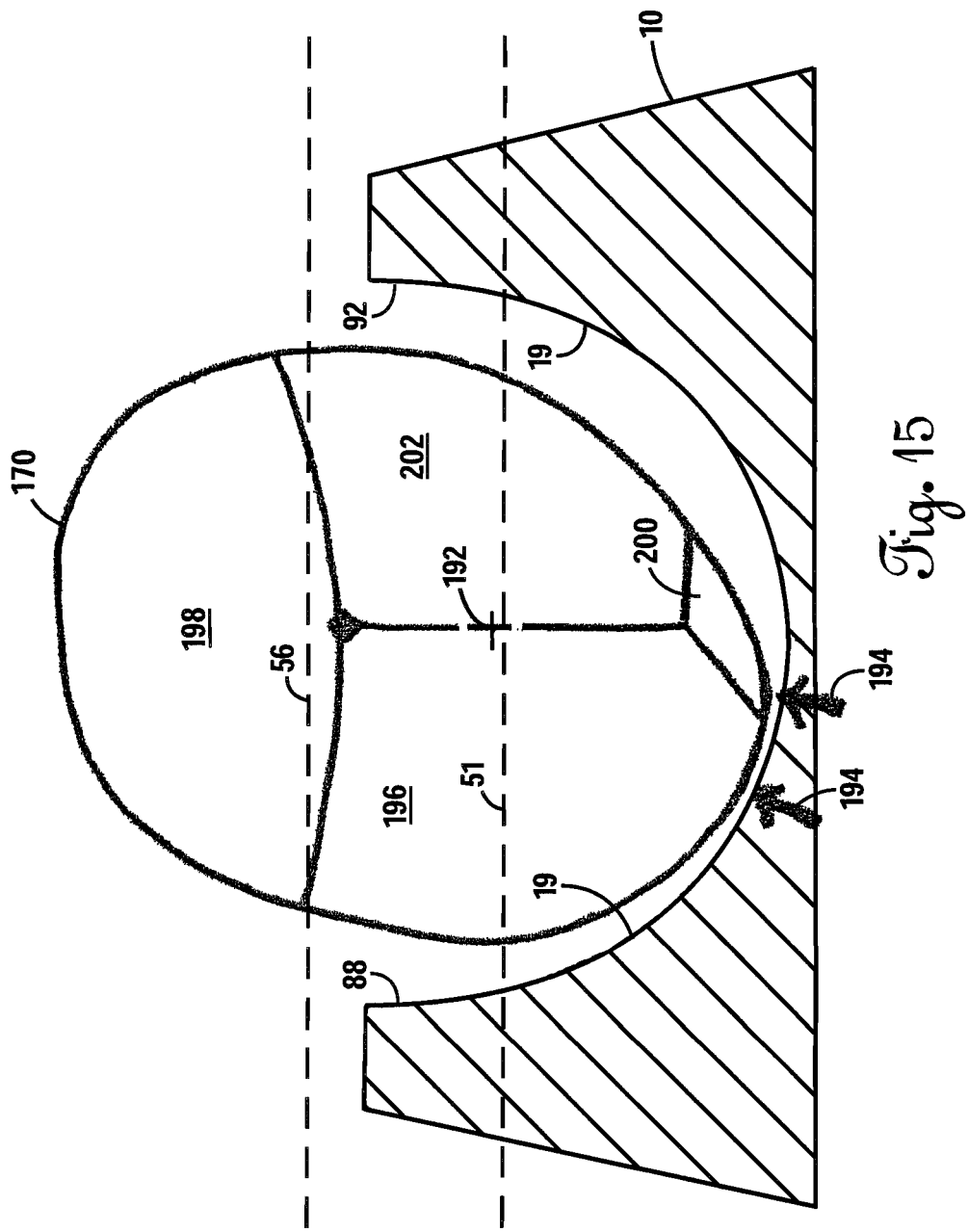
FIG. 15 is a partial sectional view of the orthosis through the inclined first plane. of FIG. 10 of a plagiocephalic cranium.

FIG. 15 is a partial sectional view of the preferred embodiment through the first plane 74 of FIG. 8 with an infant having a plagiocephalic cranium 170 with abnormal prominent growth at the left parietal bone 196 and the right side of the frontal bone 198, in addition to a flattened configuration at the right parietal bone 202 and the occipital bone 200. In the supine position shown, initial forces 194 are concentrated on the lower end of the left parietal bone 196 and left occipital bone 200. However, it should be noted that this is an unstable configuration that will inevitably lead to rotation—in this case, clockwise rotation—about the longitudinal axis 192.

FIG. 16 is a partial sectional view within the inclined first plane 74 of FIG. 10 depicting the infant having a plagiocephalic cranium 170 rotated thirty degrees clockwise about its longitudinal axis 192. In this rotated position, the contact surface 19 contacts and provides forces 194 acting on the prominent left parietal bone 196, thereby restricting further lateral growth of that prominent bone. Additionally, the second lateral support surface 92 contacts and provides forces 199 acting on the right side of the frontal bone 198 and also restricting growth in that prominent area. The contact with the second lateral support surface 92 further eliminates all external forces from the flattened occipital bone 200 and right parietal bone 202, thus redirecting growth to these bones by allowing the bones to expand. In this manner, the infant's plagiocephalic cranium 170 is allowed to grow into a normal shape.

FIG. 17 depicts the preferred embodiment in use with a brachycephalic cranium 204 having a flattened occipital bone 216 and bulging, prominent left and right parietal bones 208, 210 resting in a supine position. The contact surface 19 contacts and provides forces 206 acting on both parietal bones 208, 210 restricting lateral growth of these parietal prominences. The normal cranial shape of the contact surface 19 eliminates any contact and forces acting on the occipital bone 216. This redirects growth and expansion in a more frontal direction as well as allows the flattened occipital bone 216 to grow outward, thereby allowing for correction of the deformity over time with growth.

FIG. 18 shows the same brachycephalic cranium 204 depicted in FIG. 17 resting in the preferred embodiment of the orthosis 10 and rotated forty degrees about the longitudinal axis of the headrest 10. The contact surface 19 of the depression 18 contacts and provides forces acting on the prominent right parietal bone 210 and thereby restricts growth of that bone. At the same time, the first lateral support surface 88 contacts and provides forces 206 acting on the prominent left parietal bone 208 and, once again, restricts growth of that bone 208. The normal cranial shape of the contact surface 19 provides a gap between the contact surface 19 of the depression 18 and the flattened occipital bone 216, thereby eliminating forces acting on the occipital bone 216 and, once again, allows for outward growth in that area. The lack of contact forces acting on the frontal bone 211 also allows for forward growth to the cranium 204. In this manner, the orthosis 10 provides for correction of a brachycephalic cranium 204 resting in a rotated position.

Although the invention has thus far been described with reference to only full term infants, the principles and concepts are also applicable to a premature infant's cranium, albeit on a smaller scale. In fact, the cranial vault of a premature infant is more susceptible to development of positional deformities than a full term infant because the cranial bones are much weaker and more malleable, and the skin more fragile.

According to industry data, the mean head circumference of an infant at 26 weeks is about 23.5 centimeters, the mean head circumference of an infant at 36 weeks is roughly 33 cm, and two standard deviations on either side of this 26- to 36-week growth curves is slightly larger than ±2 cm. Thus, by simply "shrinking" the preferred embodiment described herein to accommodate this curve, the same principles are operative to correct and prevent positional deformities in premature infants in the same manner. Because of the weaker and more malleable cranial bones of a premature infant, the top surface should be softer than the top surface as described with reference to the preferred embodiment herein. The inventor has found that the hardness of the surface when used for premature infants is between 20-30 on the OO scale durometer.

Figure 20:
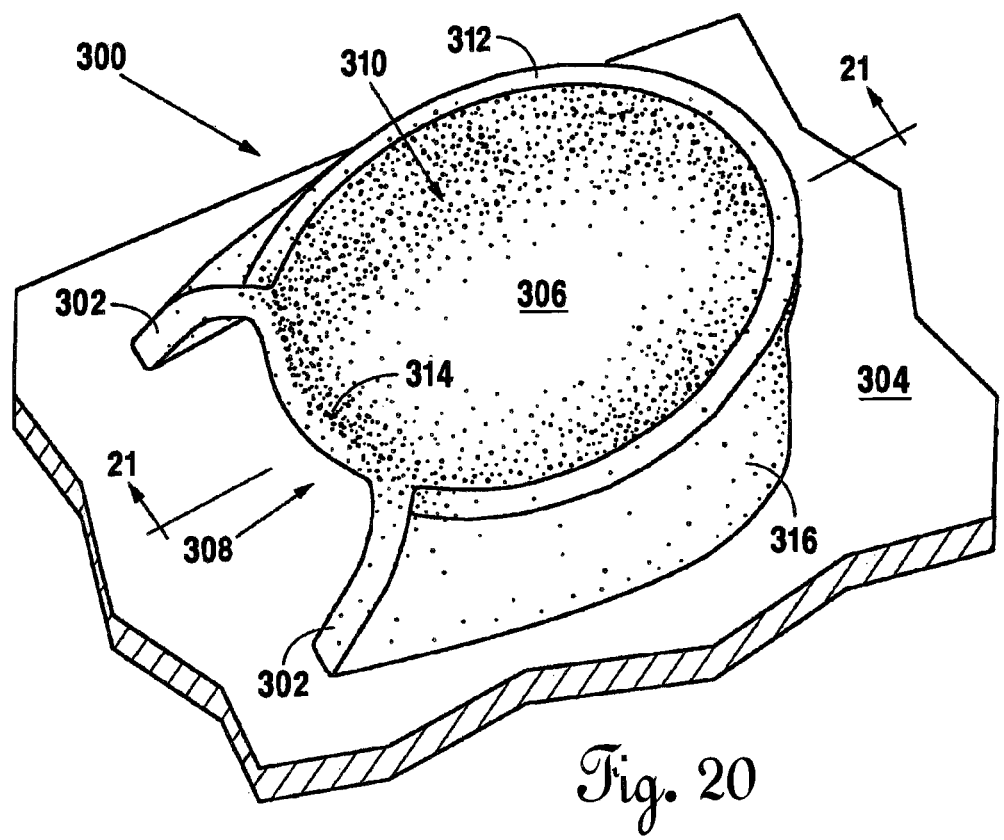
FIG. 20 is a frontal view of the craniocervical orthosis shown in FIG. 22.
Figure 19:
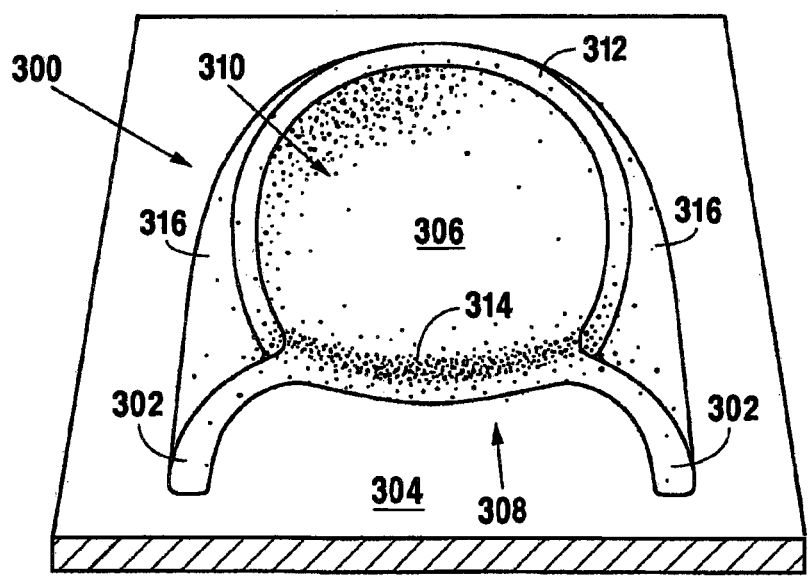
FIG. 19 is perspective view of an alternative embodiment of the present invention.
Figure 21:
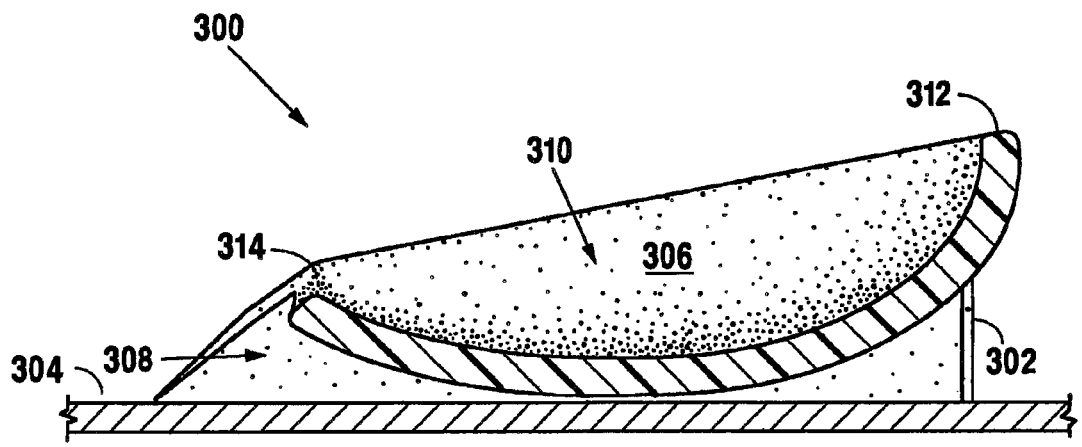
FIG. 21 is a sectional view along Line 21-21 of FIG. 19.

FIG. 19 through FIG. 21 show an alternative embodiment of the present invention that requires less material to manufacture. The headrest 300 comprises two beams 302 for contacting a resting surface 304, and a top surface 306 for contacting an infant's cranium. The elongated beams 302 are positioned along opposite sides of the headrest 300. The front and back of the headrest 300 are open, forming an opening 308 defined on either side by the beams 302.

The top surface 306 of the headrest 300 comprises a generally hemi-ellipsoidal depression 310 having the top surface 306 that corresponds to the shape of a normal infantile cranium and a rim 312 that defines a substantial portion of the depression 310. At one end of the depression 310, a ridge 314 is positioned to support the neck of the infant. The top surface 306 is preferably made of a closed cell foam material, although other materials may be used as described hereinabove. A pair of side surfaces 316, only one of which is shown by FIG. 5, adjoin the rim 312 to the beams 302.

As shown more clearly by FIG. 21, the beams 302 are positioned at opposing sides of the headrest 300 and along the perimeter thereof, thereby forming the opening 308 between the beams 302. In another embodiment, however, the opposed beams 302 can be positioned at the front and rear of the headrest 300.

After placement of the headrest 300 on the resting surface 304 so that the beams 302 are in contact therewith, the infant's head is placed in the depression 310 with the infant's head resting in the depression 310. Correction and/or prevention of the infant's abnormally shaped cranium is then accomplished in the same manner as in the preferred embodiment.

Figure 22:
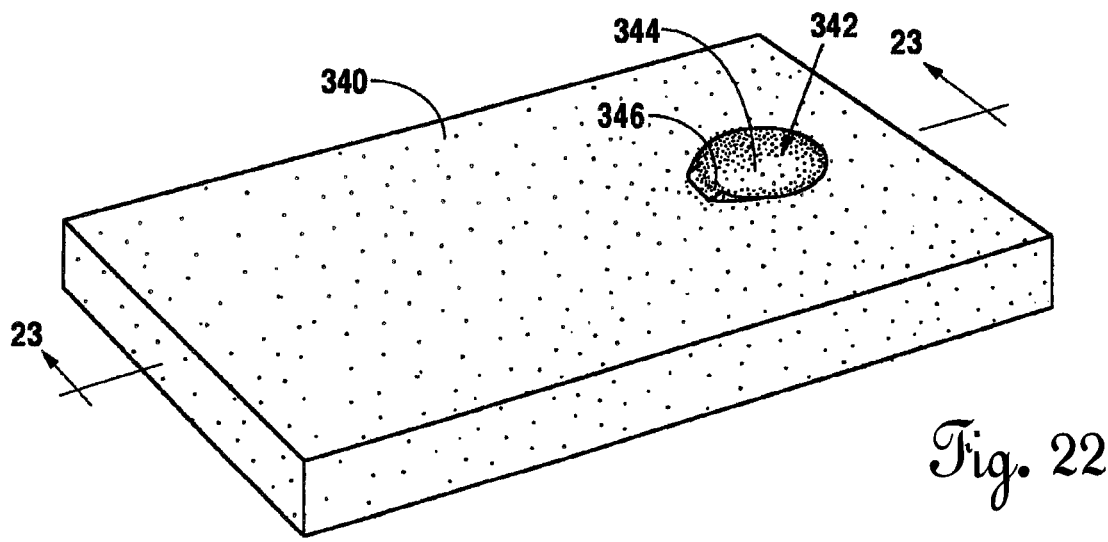
FIG. 22 is a perspective view of another alternative embodiment of the present invention.
Figure 23:
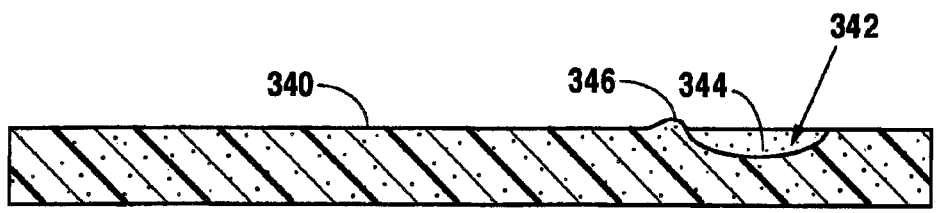
FIG. 23 is a sectional view along Line 23-23 of FIG. 22.

FIG. 22 and FIG. 23, which is a sectional view along Line 23-23 of FIG. 22, show another embodiment of the present invention. The apparatus of this embodiment comprises a mattress or padded surface 340 and a generally hemi-ellipsoidal depression 342 in a portion of the mattress surface 340. A top surface 344 in the depression 342 corresponds to the shape of a normal infantile cranium. In this embodiment, the top surface 344 of the depression 342 is semi-rigid, resilient, and made of a closed cell foam material, providing external forces acting on abnormal cranial bulges and minimizing or eliminating external forces acting on abnormal cranial depressions of the infant. However, it is anticipated that other materials could be utilized, such as open cell foam with a vinyl coating. In this embodiment, a ridge 346 at one end of the top surface 344 is shaped and positioned to support the neck of the infant while the infant's head rests on the top surface 344 of the apparatus. In another version of this embodiment, it is anticipated that the ridge 346 will be eliminated.

The embodiment shown by FIG. 22 and FIG. 23 is disclosed with a substantially flat mattress or padded surface 340. However, it is anticipated that the mattress or padded surface 32 could be contoured to prevent an infant from rolling. It is further anticipated that the area of the mattress or padded surface 340 surround the depression 342 could be raised to provide support for the infant's head in a slightly raised position.

As with the already-described embodiments, the infant's head is placed in the depression 342 formed in the mattress 340 such that the infant's head is in contact with the top surface 344. The infant's neck is supported by the ridge 346, while the infant's body is supported in a comfortable resting position by the mattress 340 in a generally supine position. Correction and/or prevention of the infant's abnormally shaped cranium is then accomplished in the same manner as in the preferred embodiment.

Figure 24:
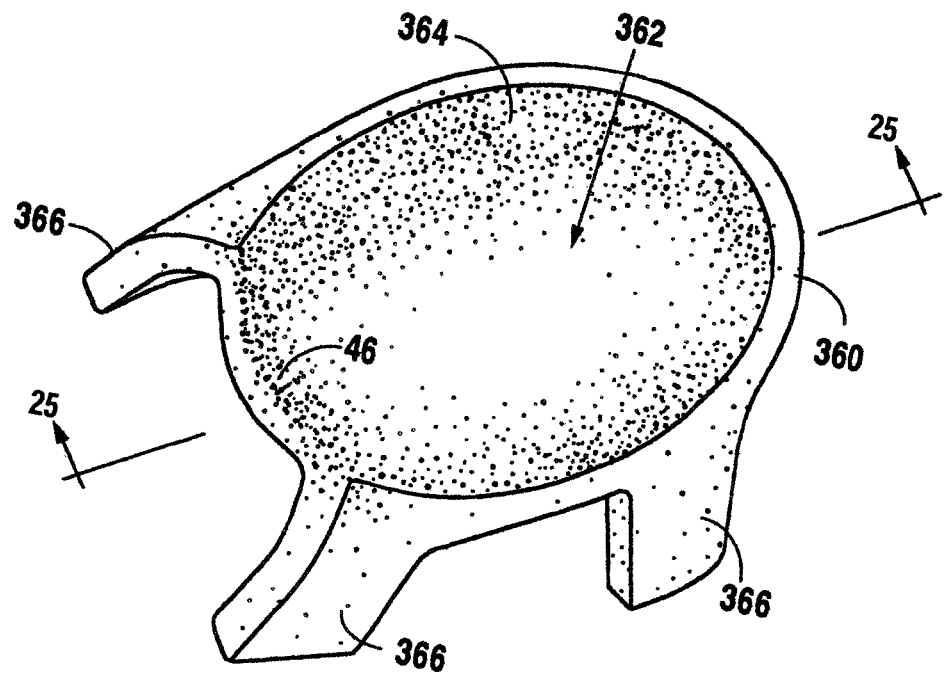
FIG. 24 is yet another embodiment of the present invention.
Figure 25:
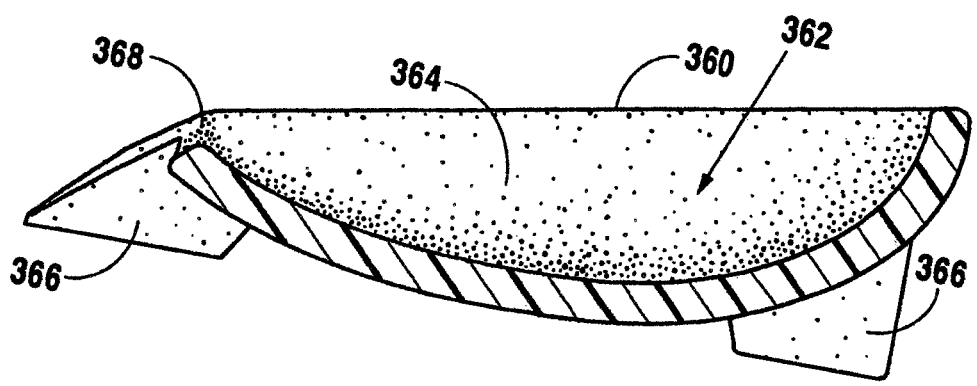
FIG. 25 is a sectional view along Line 25-25 of FIG. 24.

FIG. 24 and FIG. 25, which is a sectional view along Line 25-25 of FIG. 24, show another embodiment of the present invention, an apparatus comprised of a semi-rigid body 360 with a hemi-ellipsoidal depression 362 having a contact surface 364 that is in the shape of a normal infantile cranium. A plurality of legs 366 support the semi-rigid body 360 in a position to allow an infant's head to rest on the contact surface 364. In this embodiment, there are four legs 366, as shown in FIG. 24 and FIG. 25. However, it is anticipated that more or fewer legs could be used to support the body 360. The contact surface 364 is resilient and made of closed cell foam, although in alternative embodiments of the present invention the contact surface 364 may be made of other material, including open cell foam covered with a vinyl coating and other materials as described hereinabove. Furthermore, a ridge 368 at one end of the contact surface 364 is shaped and positioned to support the neck of the infant while the infant's head rests on the contact surface 364 of the apparatus.

After placement of the apparatus on a resting surface so that legs 366 are in contact therewith, the infant's head is placed in the depression 362 with the infant's head resting on the contact surface 364 and the infant's neck being supported by the ridge 368. Correction and/or prevention of the infant's abnormally shaped cranium is then accomplished in the same manner as in the preferred embodiment.

It should be noted that the smaller the infant cranium, the more angular rotation of the cranium about the longitudinal axis is required to contact one of the lateral support surfaces. In other words, generally speaking, a smaller infant cranium placed in a given headrest and depression will require more rotation about the longitudinal axis than a larger, similarly-shaped cranium positioned in the same headrest and depression. However, it is desirable that rotation of an infant's cranium located within a depression be limited to approximately the range of angular rotation described with reference to the foregoing figures. Although this concern could be addressed by manufacturing the headrest in various sizes to correspond to the range of expected cranial sizes as set forth supra, for commercialization, it is desirable for cost reduction purposes that fewer variations of the present invention be produced to take advantage of manufacturing economies of scale.

Figure 26:
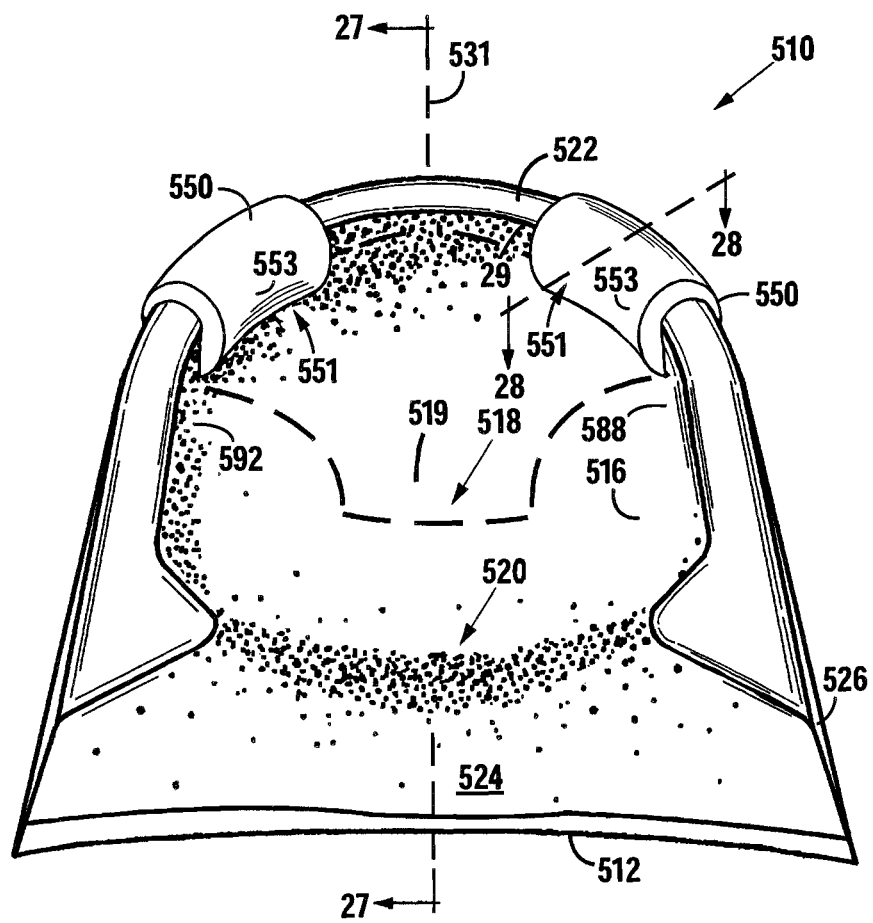
FIGS. 26 is a front perspective view of yet another alternative embodiment of the present invention that comprises two spacing members positioned on the rim.
Figure 27:
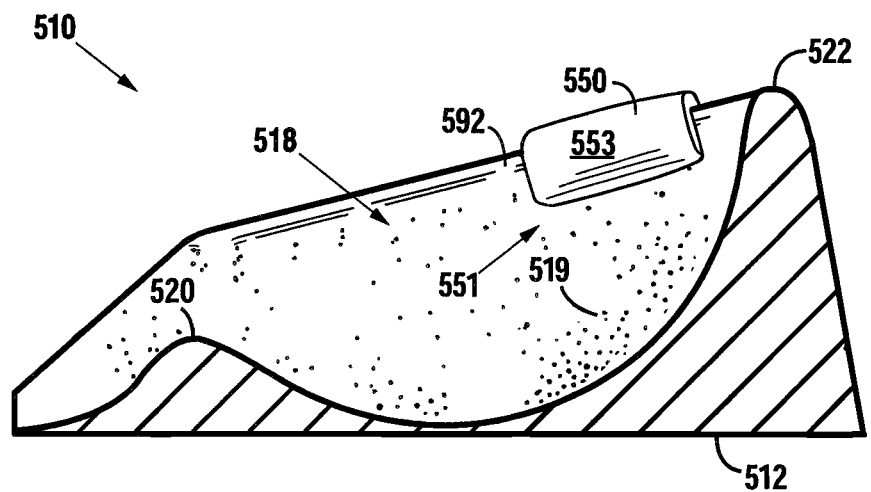
FIG. 27 is a side sectional elevation through Line 27-27 of FIG. 26.
Figure 28:
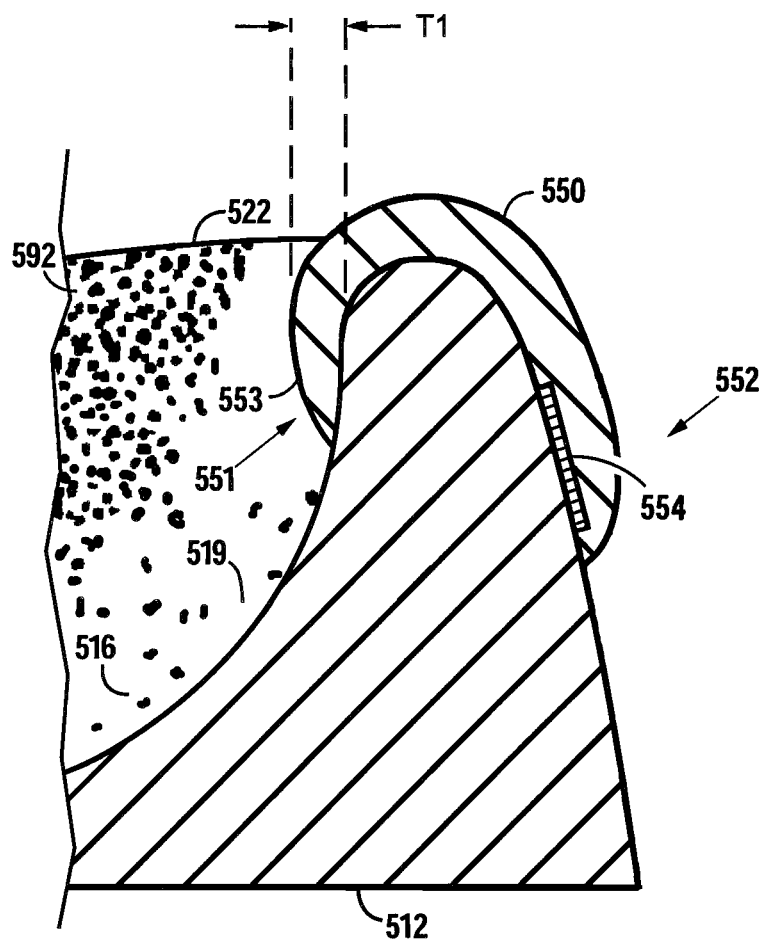
FIG. 28 is a sectional elevation through Line 28-28 of FIG. 26.

This conflict between manufacturing preference and patient treatment preference can be addressed, however, by providing for adjustability of the positions of the lateral support surfaces, thus allowing rotation of the cranium to be limited as desired based on the size of the cranium. For example, FIG. 26 through FIG. 28 show another embodiment of a headrest 510 having the features of the present invention wherein the position of the lateral support surfaces is adjustable to accommodate various cranium sizes (i.e., limit the range of possible rotation of the cranium within the depression). FIG. 26 is a front perspective view of the embodiment. FIG. 27 and FIG. 28 are sectional views through ine 27-27 and Line 28-28, respectively, of FIG. 26.

As referenced with respect to the previously-described embodiments, the headrest 510 of this alternative embodiment comprises a bottom surface 512, and a top surface 516 for contacting an infant's cranium. The top surface 516 comprises a generally hemi-ellipsoidal depression 518, a contact surface 519 that corresponds to the shape of a normal infantile cranium, and a rim 522 defining a substantial portion of the depression 518. A ridge 520 is positioned at one end of the depression 518 to support the neck of the infant. The top surface 516 is preferably made of a closed cell foam material, but may alternatively be made of open cell foam material covered with a vinyl or other surface coating, closed cell foam layered over higher density foam, open cell foam layered over higher density foam, or closed cell foam layered over a more rigid solid or hollow plastic. A curved front surface 524 is positioned to cradle the infant's shoulders and support the neck of the infant while the infant's cranium is in contact with the top surface 516. A preferably-curved side surface 526 extends between the rim 522 and the bottom surface 512.

Two attachable spacing members 550 are positioned over the rim 522 and preferably centered at preferably approximately sixty degrees from the longitudinal axis 531. Preferably, the spacing members 550 are substantially U-shaped and sized to fit snugly over the rim 522, and each has a first leg 551 which extends into the depression 518 and contacts the lateral support surfaces 588, 592, and a second leg 552 extending downward adjacent to and contacting the sidewall 526 of the headrest 510. The spacing members 550 are made of a closed cell foam material, but may alternatively be made of open cell foam material covered with a vinyl or other surface coating, closed cell foam layered over higher density foam, open cell foam layered over higher density foam, or closed cell foam layered over a more rigid solid or hollow plastic.

As shown in FIG. 28, in this specifically-described embodiment, the outer portion 552 of the spacing member 550 is removeably attached to the body of the headrest 510 with a hook-and-loop fastener 554. Alternative embodiments contemplate other fastening hardware and adhesives. Placement of the spacing members 550 on the rim 522 provides the ability to alter the rotation range of the infant's head when placed in the headrest 510.

Normal operation for correction of an abnormally shaped infant cranium is as referenced with respect to the previously-described embodiments. The headrest 510 is placed on a resting surface (not shown) so that the bottom surface 512 is in contact therewith. The infant's head is then placed in the depression 518 with the infant's cranium resting on the contact surface 519. The effective distance between the lateral support surfaces 588, 592 can be altered by attaching one or more of the spacing members 550 for proper fitting of the infant's cranium within the headrest 510. In this specific embodiment, it is preferred that the maximum thickness T1 of the leg 551 of the spacing members 550 extending into the depression 518 and along a sagittal axis is approximately eight millimeters.

Initially, the posterior and part of the side aspects of the infant's head contact the contact surface 519, although during the sleep period the infant's head may roll to one side or the other. When this occurs, the side of the infant's head will contact the interior surface 553 of the first leg 551 of one of the spacing members 550. In this manner, the interior surface 553 acts as an adjusted lateral support surface. Throughout the sleep period, the infant's neck is supported by the ridge 520. The infant's shoulders are aligned in and cradled by the curved front surface 524. As the infant's head makes contact with the top surface 516, the contact surface 519 provides external forces acting on any abnormal bulges of the infant's cranium and reduces or eliminates external forces that act on abnormal depressions (flattened areas) of the infant's cranium. As referenced with respect to the previously described embodiments, this contact reduces the net outward forces from brain and skull growth at these prominences, and redirects the growth to areas of the cranium where the infant's head is not in contact with the top surface 516. As the infant's cranium grows, the spacing members 550 can be removed or replaced with spacing members having a thinner first leg 551.

Although in this embodiment the spacing members 550 are described as being substantially U-shaped, it is anticipated that the spacing members 550 could have varying shapes and attachment locations on the headrest 510. For example, the spacing members 550 could be a circular or rectangular pad having a flat interior surface to act as an adjusted lateral support surface and a flat exterior surface for adhesion to the lateral support surfaces of the headrest.

Figure 29:
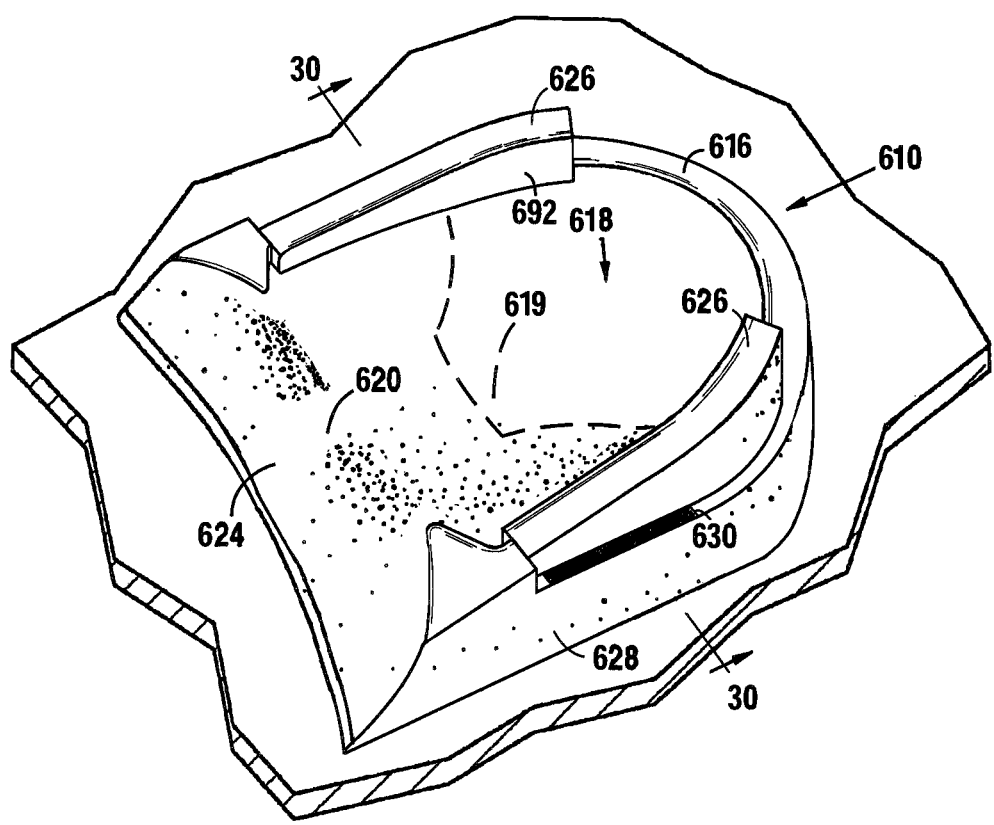
FIG. 29 is a front perspective view of still another embodiment of the present invention wherein the lateral support surfaces are laterally adjustable.
Figure 30:
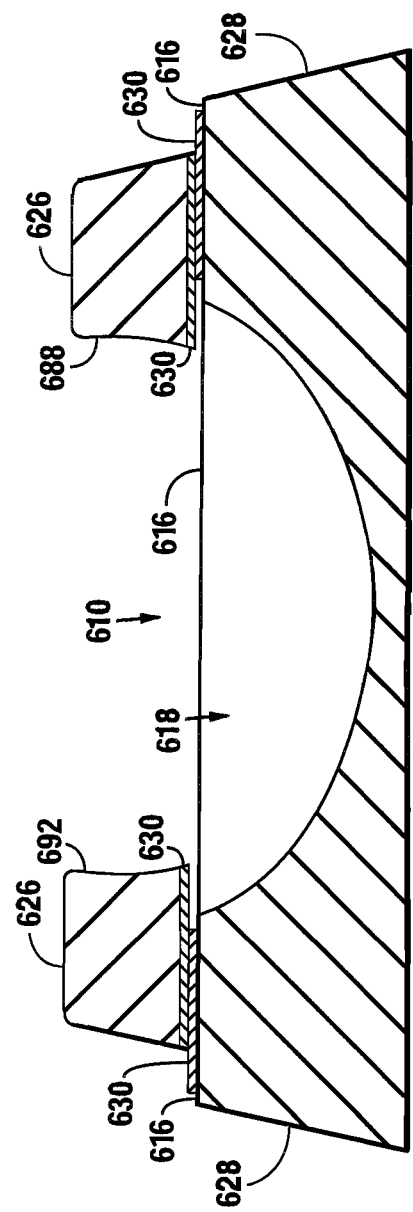
FIG. 30 is a rear section view through plane 30-30 of FIG. 29.

FIG. 29 and FIG. 30 show an alternative embodiment of a "low profile" headrest 610 with first and second laterally adjustable siderails 626. FIG. 29 is a perspective view of the embodiment, while FIG. 30 is a rear section view through plane 30-30 of FIG. 29. The "low profile" headrest 610, as described supra, is provided that otherwise has some of the features of the present invention, such as the top surface 616, depression 618, and the like. However, as discussed supra, this "low profile" headrest 610 does not itself provide lateral support with lateral support surfaces.

As shown in FIG. 29 and FIG. 30, the laterally-adjustable siderails 626 are fixable to the top surface 616 of the "low profile" headrest 610 with hook-and-loop 630 or other fastening methodology and positioned to provide lateral support to an infant's cranium resting in the headrest 610 with lateral support surfaces 688, 692 on the interior sidewalls of the siderails 626. The laterally adjustable siderails 626 are positioned such that the lateral support surfaces 688, 692 are positioned anterior of the first coronal plane and superior to the mid-cranial transverse plane, as described with reference to the other embodiments. The first and second lateral support surfaces 688, 692 do not extend anteriorly of the second coronal plane, as providing a completely unobstructed visual field is imperative to eliminate the risk of iatrogenic-induced neuro-opthalmological injury (i.e., obstructive amblyopia). In addition, the laterally-adjustable siderails 626 allow for adjustment of the distance between the lateral support surfaces 688, 692 by repositioning both laterally-adjustable siderails 626 toward the infantile cranium and reattaching them to the top surface 616.

The present invention is described above in terms of a preferred illustrative embodiment of a specifically described headrest, as well as alternative embodiments of the present invention. Those skilled in the art will recognize that alternative constructions of such a headrest can be used in carrying out the present invention. Other aspects, features, and advantages of the present invention may be obtained from a study of this disclosure and the drawings, along with the appended claims.

I claim:

1. An orthotic headrest for promoting normal shaping of the cranium of an infant, the headrest comprising:
   a bottom surface for contact with a resting surface;
   a top surface;
   a generally hemi-ellipsoidal depression in said top surface, said depression having a nadir;
   a contact surface in said depression having the shape of at least a portion of a normal infantile cranium;
   a ridge at one end of said depression for supporting the neck of said infant; and
   first and second lateral support surfaces having at least a portion positioned anterior of a first coronal plane and superior to a mid-cranial transverse plane;
   said contact surface comprising at least a portion of said first and second lateral support surfaces;
   wherein said headrest prevents plagiocephaly and brachycephaly from developing in said infant's normal cranium resting in a supine position by restricting lateral expansion of the parietal bones with said first and second lateral support surfaces and said contact surface below said first and second lateral support surfaces.

2. The orthotic headrest of claim 1 wherein said top surface is semi-rigid.

3. The orthotic headrest of claim 2 wherein the hardness of said top surface is between 65 and 75 (inclusive) on a OO durometer scale.

4. The orthotic headrest of claim 1 wherein said contact surface has the shape of a portion of a normal infant cranium having a circumference between 36.5 and 46.5 centimeters, inclusive.

5. The orthotic headrest of claim 1 wherein said first and second lateral support surfaces do not extend anteriorly of a second coronal plane.

6. The orthotic headrest of claim 1 wherein at least a portion of said first and second lateral support surfaces are substantially vertical.

7. The orthotic headrest of claim 1 wherein said contact surface comprises at least the area of the top surface that (1) is superior to a diagonal plane angle 45-degrss from vertical in the superior direction and intersecting said nadir; and (2) is posterior of a third coronal plane.

8. The orthotic headrest of claim 1 wherein said contact surface comprises the area of the top surface that (1) is superior to an inclined first plane angled between 10 and 20 degrees superior of said mid-cranial transverse plane and intersecting said nadir; and (2) is posterior of a third coronal plane.

9. The orthotic headrest of claim 1 wherein said first and second lateral support surfaces are positioned such that rotation about the longitudinal axis of a properly-positioned, normal infant cranium results in contact of the frontal bone of said normal infant cranium with one of said first and second lateral support surfaces superior of the mid-cranial transverse plane.

10. The orthotic headrest of claim 9 wherein said contact with the frontal bone of said normal infantile cranium occurs when the circumference of said cranium is between 36.5 and 46.5 cm, inclusive.

11. The orthotic headrest of claim 10 wherein said contact surface of said depression is shaped and positioned such that it contacts the occipital bone and the parietal bone which is nearest to the point of contact with the frontal bone.

12. The orthotic headrest of claim 1 wherein said depression further comprises a middle portion that gradually widens from said middle portion's superior end to its inferior end providing space for the ears of a normally-shaped infant's cranium.

13. The orthotic headrest of claim 1 wherein said headrest prevents brachycephaly from developing in said infant's normal cranium which is resting in a rotated position about a longitudinal axis by restricting lateral growth of the left and right parietal bones with said first or second lateral support surface and said contact surface of said depression below said first and second lateral support surfaces.

14. The orthotic headrest of claim 1 wherein said headrest prevents plagiocephaly from developing in said infant's normal cranium resting in a rotated position about a longitudinal axis by restricting lateral growth on the parietal bones with said contact surface of said depression below said first and second lateral support surfaces on the side of said cranium opposite said direction of rotation and lateral and frontal growth of the frontal bone with said lateral support surface on the same side as said direction of rotation.

15. The orthotic headrest of claim 1 wherein:
    said contact surface provides external forces acting on abnormal cranial bulges of said infant's cranium; and
    said contact surface eliminates external forces action on abnormal cranial depressions of said infant's cranium.

16. The orthotic headrest of claim 1 wherein said headrest corrects brachycephaly in an infant's cranium resting within said headrest in a nonrotated supine position by:
    restricting lateral growth of prominent left and right parietal bones; and
    promoting posterior growth of said occipital bone by eliminating contact between said headrest and said occipital bone of said infant's cranium.

17. The orthotic headrest of claim 1 wherein said headrest corrects plagiocephaly in an infant's cranium resting in a rotated position about a longitudinal axis by promoting growth of the flattened occipital and parietal bones by eliminating contact between said headrest and the flattened occipital and parietal bones, and by restricting growth of a prominent frontal bones by contact between said prominent frontal and parietal bones and one of said first and second lateral support surfaces and of a prominent parietal bone by contact between said prominent parietal bone and said contact surface below said first and second lateral support surfaces.

18. The orthotic headrest of claim 1 wherein said headrest corrects scaphocephaly in an infant's cranium resting in a rotated position about a longitudinal axis by promoting growth of flattened parietal bones by eliminating contact between said contact surface and said flattened left and right parietal bones and restricting growth of a prominent occipital bone by contact between the prominent occipital bone and the contact surface.

19. The orthotic headrest of claim 1 wherein said headrest corrects brachycephaly in an infant's cranium resting in a rotated position about a longitudinal axis by:
    promoting growth of a flattened occipital bone and flattened posterior end of the left and right parietal bones by eliminating contact between said contact surface and said flattened occipital and flattened posterior end of the left and right parietal bones; and
    restricting growth of prominent mid and anterior parietal bones with contact between a prominent mid and anterior parietal bone opposite the direction of rotation and one of said first and second lateral support surfaces and between a prominent mid and anterior parietal bone in the direction of rotation and the contact surface below said first and second lateral support surfaces.

20. An orthotic headrest for promoting normal shaping of the cranium of an infant, the headrest comprising:
    a bottom surface for contact with a resting surface;
    a top surface;
    a generally hemi-ellipsoidal depression in said top surface, said depression having a nadir;
    a contact surface in said depression having the shape of at least a portion of a normal infantile cranium;
    said contact surface comprising the area of the top surface that is superior to an inclined first plane angled between 10 and 20 degrees superior of said mid-cranial transverse plane and intersecting said nadir and is posterior of a third coronal plane;
    a ridge at one end of said depression for supporting the neck of said infant; and
    first and second lateral support surfaces having at least a portion positioned anterior of a first coronal plane and superior to a mid-cranial transverse plane;
    said contact surface comprising at least a portion of said first and second lateral support surfaces.

21. An orthotic headrest for promoting normal shaping of the cranium of an infant, the headrest comprising:
    a bottom surface for contact with a resting surface;
    a top surface;
    a generally hemi-ellipsoidal depression in said top surface, said depression having a nadir;
    a contact surface in said depression having the shape of at least a portion of a normal infantile cranium;
    a ridge at one end of said depression for supporting the neck of said infant; and
    first and second lateral support surfaces having at least a portion positioned anterior of a first coronal plane and superior to a mid-cranial transverse plane;
    said contact surface comprising at least the surface area of said depression that is (1) superior to an inclined plane angled 20 degrees superior of the mid-cranial transverse plane and intersecting said nadir, and (2) posterior of a third coronal plane;
    said contact surface comprising at least a portion of said first and second lateral support surfaces.

22. An orthotic headrest for promoting normal shaping of the cranium of an infant, the headrest comprising:
    a bottom surface for contact with a resting surface;
    a top surface;
    a generally hemi-ellipsoidal depression in said top surface, said depression having a nadir;
    a contact surface in said depression having the shape of at least a portion of a normal infantile cranium;
    a ridge at one end of said depression for supporting the neck of said infant; and
    first and second lateral support surfaces having at least a portion positioned anterior of a first coronal plane and superior to a mid-cranial transverse plane;
    said mid-cranial transverse plane being seven to eight cm from the most superior point of contact of an infant's normally-shaped cranium of 46.5 cm in circumference when said cranium is supinely positioned in the headrest;
    said contact surface comprising at least a portion of said first and second lateral support surfaces.

23. An orthotic headrest for promoting normal shaping of the cranium of an infant, the headrest comprising:
    a bottom surface for contact with a resting surface;
    a top surface;

a generally hemi-ellipsoidal depression in said top surface, said depression having a nadir;

a contact surface in said depression having the shape of at least a portion of a normal infantile cranium;

a ridge at one end of said depression for supporting the neck of said infant; and first and second lateral support surfaces having at least a portion positioned anterior of a first coronal plane and superior to a mid-cranial transverse plane;

said contact surface comprising at least a portion of said first and second lateral support surfaces;

at least one spacing member attachable to said headrest having a portion of said spacing member extending into said hemi-ellipsoidal depression adjacent at least one of said first and second lateral support surfaces.

24. The orthotic headrest of claim 23 wherein said at least one spacing member is removably attachable and comprises a first leg that extends into the depression and contacts the lateral supports surface and a second leg extending downward adjacent to and contacting the sidewall of the headrest.

25. The orthotic headrest of claim 24 wherein said at least one spacing member comprises two spacing members centered at approximately sixty degrees from the longitudinal axis.

26. An orthotic headrest for promoting normal shaping of the cranium of an infant, the headrest comprising:

a bottom surface for contact with a resting surface;

a top surface;

a generally hemi-ellipsoidal depression in said top surface, said depression having a nadir;

a contact surface in said depression having the shape of at least a portion of a normal infantile cranium;

a ridge at one end of said depression for supporting the neck of said infant; and first and second lateral support surfaces having at least a portion positioned anterior of a first coronal plane and superior to a mid-cranial transverse plane;

said contact surface comprising at least a portion of said first and second lateral support surfaces;

at least one laterally adjustable siderail having at least one internal sidewall, said at least one laterally adjustable siderail being fixable to said top surface to provide lateral support to an infant's cranium resting in the headrest.

27. The orthotic headrest of claim 26 wherein said at least one laterally adjustable siderail comprises at least a portion of each of said first and second lateral support surfaces on said at least one interior sidewall.

28. A craniocervical orthosis for promoting normal shaping of the cranium of an infant, said craniocervical orthosis comprising:

a bottom surface for contact with a resting surface;

a top surface having a contact surface for contact with said cranium of said infant, said contact surface being shaped like at least a portion of the curvature of a normal infant cranium;

first and second lateral support surfaces each having at least a portion extending anteriorly of a first coronal plane at a position superior to a mid-cranial transverse plane and between 6.2 and 6.7 cm, inclusive, from a nadir of said contact surface;

said contact surface comprising at least a portion of said first and second lateral support surfaces;

a ridge at one end of said top surface for supporting the neck of said infant;

said nadir being positioned at the intersection of said mid-cranial transverse plane and said contact surface.

29. The craniocervical orthosis of claim 28 wherein said contact surface is shaped like at least a portion of the curvature of a normal infant cranium having a circumference between 36.5 cm and 46.5 cm, inclusive.

30. The craniocervical orthosis of claim 28 wherein said contact surface comprises at least the surface area that is (1) superior to a diagonal plane angled 45-degrees from vertical in the superior direction and intersecting said nadir, and (2) posterior of a third coronal plane.

31. The craniocervical orthosis of claim 28 wherein said contact surface comprises at least the surface area that is (1) superior to an inclined first plane angled 20 degrees superior of the mid-cranial transverse plane and intersecting said nadir, and (2) posterior of a third coronal plane.

32. The craniocervical orthosis of claim 28 wherein said mid-cranial transverse plane is seven to eight cm from the most superior point of contact of an infant's normally-shaped cranium 46.5 cm in circumference when said cranium is supinely positioned in the orthosis.

33. A craniocervical orthosis for promoting normal shaping of the cranium of an infant, said craniocervical orthosis comprising:

a bottom surface for contact with a resting surface;

a top surface having a contact surface for contact with said cranium of said infant, said contact surface being shaped like at least a portion of the curvature of a normal infant cranium;

first and second lateral support surfaces each having at least a portion extending anteriorly of a first coronal plane at a position superior to a mid-cranial transverse plane;

said contact surface comprising at least a portion of said first and second lateral support surfaces;

the most superior point of contact with the contact surface for a normally-shaped infant cranium of 46.5 cm circumference resting in a supine position being between 8.0 and 8.6 cm from said bottom surface.

a ridge at one end of said top surface for supporting the neck of said infant;

a nadir at the intersection of said mid-cranial transverse plane and said contact surface.

34. A craniocervical orthosis for promoting normal shaping of the cranium of an infant, said craniocervical orthosis comprising:

a bottom surface for contact with a resting surface;

a top surface having a contact surface for contact with said cranium of said infant, said contact surface being shaped like at least a portion of the curvature of a normal infant cranium;

first and second lateral support surfaces each having at least a portion extending anteriorly of a first coronal plane at a position superior to a mid-cranial transverse plane;

said first and second lateral support surfaces do not extend anteriorly of a second coronal plane;

said contact surface comprising at least a portion of said first and second lateral support surfaces;

a ridge at one end of said top surface for supporting the neck of said infant;

a nadir at the intersection of said mid-cranial transverse plane and said contact surface.

35. The craniocervical orthosis of claim 34 wherein said second coronal plane is between 8.8 and 9.3 centimeters, inclusive from said nadir.

36. An orthotic headrest for promoting normal shaping of the cranium of an infant, the headrest comprising:

a bottom surface for contact with a resting surface;

a top surface;

a generally hemi-ellipsoidal depression in said top surface, said depression having a nadir;

a contact surface in said depression having the shape of at least a portion of a normal infantile cranium;

said contact surface comprising at least the area of the top surface that is superior to a diagonal plane angled 45 degrees from vertical in the superior direction and is intersecting said nadir and is posterior of a third coronal plane;

a ridge at one end of said depression for supporting the neck of said infant; and first and second lateral support surfaces having at least a portion positioned anterior of a first coronal plane and superior to a mid-cranial transverse plane;

said contact surface comprising at least a portion of said first and second lateral support surfaces.

37. A craniocervical orthosis for promoting normal shaping of the cranium of an infant, said craniocervical orthosis comprising:

a bottom surface for contact with a resting surface;

a top surface having a contact surface for contact with said cranium of said infant, said contact surface being shaped like at least a portion of the curvature of a normal infant cranium;

first and second lateral support surfaces each having at least a portion extending anteriorly of a first coronal plane at a position superior to a mid-cranial transverse plane;

said contact surface comprising at least a portion of said first and second lateral support surfaces;

a ridge at one end of said top surface for supporting the neck of said infant;

a nadir at the intersection of said mid-cranial transverse plane and said contact surface;

said nadir being between 0.3 and 0.7 cm from the bottom surface, inclusive.

38. The craniocervical orthosis of claim 37 wherein the ridge crest is between 2.5 and 3.5 cm from the bottom surface, inclusive.

39. The craniocervical orthosis of claim 37 wherein the nadir is between six and seven cm, inclusive, from the midpoint ridge measured along the longitudinal axis of the orthosis.

40. The craniocervical orthosis of claim 37 wherein the ridge is between 12.8 and 13.8 cm in width.

41. A craniocervical orthosis for promoting normal shaping of the cranium of an infant, said craniocervical orthosis comprising:

a bottom surface for contact with a resting surface;

a top surface having a contact surface for contact with said cranium of said infant, said contact surface being shaped like at least a portion of the curvature of a normal infant cranium;

first and second lateral support surfaces each having at least a portion extending anteriorly of a first coronal plane at a position superior to a mid-cranial transverse plane;

said contact surface comprising at least a portion of said first and second lateral support surfaces;

a ridge at one end of said top surface for supporting the neck of said infant;

a nadir at the intersection of said mid-cranial transverse plane and said contact surface;

an arced rear portion and a middle portion adjacent said arced portion wherein:

the largest width of the arced rear portion is between 12.2 and 13.2 cm;

the largest width of the middle portion is between 15.8 and 16.8 cm; and the depth of the middle portion is between 7.7 and 8.3 cm.

42. The craniocervical orthosis of claim 41 wherein the greatest distance between the middle portion and a rim of the arced portion measured along the longitudinal axis is between 3.4 and 4.4 cm.

43. The craniocervical orthosis of claim 42 wherein the greatest distance between the arced portion and crest of the ridge measured along the longitudinal axis is between 9.8 and 10.5 cm.

44. A craniocervical orthosis for promoting normal shaping of the cranium of an infant, said craniocervical orthosis comprising:

a bottom surface for contact with a resting surface;

a top surface having a contact surface for contact with said cranium of said infant, said contact surface being shaped like at least a portion of the curvature of a normal infant cranium;

first and second lateral support surfaces each having at least a portion extending anteriorly of a first coronal plane at a position superior to a mid-cranial transverse plane;

said contact surface comprising at least a portion of said first and second lateral support surfaces;

a ridge at one end of said top surface for supporting the neck of said infant;

a nadir at the intersection of said mid-cranial transverse plane and said contact surface;

at least one spacing member attachable to said orthosis having a portion of said spacing member extending into a hemi-ellipsoidal depression adjacent at least one of said first and second lateral support surfaces.

45. The craniocervical orthosis of claim 44 wherein said at least one spacing member is removably attachable and comprises a first leg that extends into said depression and contacts the lateral supports surface and a second leg extending downward adjacent to and contacting the sidewall of the orthosis.

46. The craniocervical orthosis of claim 44 wherein said at least one spacing member is two spacing members positioned on opposing sides of a longitudinal axis of said depression extending from the back to the front of said orthosis.

47. A craniocervical orthosis for promoting normal shaping of the cranium of an infant, said craniocervical orthosis comprising:

a bottom surface for contact with a resting surface;

a top surface having a contact surface for contact with said cranium of said infant, said contact surface being shaped like at least a portion of the curvature of a normal infant cranium;

first and second lateral support surfaces each having at least a portion extending anteriorly of a first coronal plane at a position superior to a mid-cranial transverse plane;

said contact surface comprising at least a portion of said first and second lateral support surfaces;

a ridge at one end of said top surface for supporting the neck of said infant;

a nadir at the intersection of said mid-cranial transverse plane and said contact surface;

at least one laterally adjustable siderail having at least one internal sidewall, said at least one laterally adjustable siderail being fixable to said top surface to provide lateral support to an infant's cranium resting in the orthosis.

48. The craniocervical orthosis of claim 47 wherein said at least one laterally adjustable siderail comprises at least a portion of each of said first and second lateral support surfaces on said at least one interior sidewall.

* * * * *